United States Patent
Pagis

(10) Patent No.: US 11,737,960 B2
(45) Date of Patent: Aug. 29, 2023

(54) USE OF A PARTICULATE MINERAL TO REDUCE POLLUTION

(71) Applicant: IMERTECH SAS, Paris (FR)

(72) Inventor: Laure Pagis, Toulouse (FR)

(73) Assignee: Imertech SAS, Paris (FR)

( * ) Notice: Subject to any disclaimer, the term of this patent is extended or adjusted under 35 U.S.C. 154(b) by 3 days.

(21) Appl. No.: 16/486,548

(22) PCT Filed: Feb. 16, 2018

(86) PCT No.: PCT/EP2018/053947
§ 371 (c)(1),
(2) Date: Aug. 16, 2019

(87) PCT Pub. No.: WO2018/150002
PCT Pub. Date: Aug. 23, 2018

(65) Prior Publication Data
US 2021/0128428 A1    May 6, 2021

(30) Foreign Application Priority Data

Feb. 17, 2017 (EP) ..................................... 17305177

(51) Int. Cl.
*A61K 8/25* (2006.01)
*A61K 8/02* (2006.01)
(Continued)

(52) U.S. Cl.
CPC .............. *A61K 8/25* (2013.01); *A61K 8/0241* (2013.01); *A61K 8/042* (2013.01); *A61K 8/06* (2013.01);
(Continued)

(58) Field of Classification Search
CPC ........ A61K 8/042; A61K 8/25; A61K 8/0225; A61K 8/06; A61K 8/99; A61K 8/965;
(Continued)

(56) References Cited

U.S. PATENT DOCUMENTS

| 4,847,267 A | 7/1989 | Deckner et al. |
| 5,253,660 A | 10/1993 | Dixit et al. |

(Continued)

FOREIGN PATENT DOCUMENTS

| CN | 103619415 A | 3/2014 |
| CN | 104411286 A | 3/2015 |

(Continued)

OTHER PUBLICATIONS

ClearOFF Mineral, "Diatomaceous Earth Specifications", 2010, download from https://www.clearoffminerals.com/de-specs on Jul. 30, 2021. (Year: 2010).*

(Continued)

*Primary Examiner* — Jianfeng Song
(74) *Attorney, Agent, or Firm* — Finnegan, Henderson, Farabow, Garrett & Dunner, LLP

(57) ABSTRACT

The use of a particulate mineral as an anti-pollution agent in a composition for application to skin and/or keratin materials, a method for protecting skin and/or keratin materials from pollution, a composition comprising a particulate mineral and a method of making said composition.

9 Claims, 6 Drawing Sheets

(51) Int. Cl.

| | | |
|---|---|---|
| *A61K 8/19* | (2006.01) | |
| *A61K 8/96* | (2006.01) | |
| *A61K 8/26* | (2006.01) | |
| *A61K 8/99* | (2017.01) | |
| *A61Q 17/00* | (2006.01) | |
| *A61Q 19/00* | (2006.01) | |
| *A61Q 19/10* | (2006.01) | |
| *A61Q 5/12* | (2006.01) | |
| *A61Q 5/02* | (2006.01) | |
| *A61K 8/04* | (2006.01) | |
| *A61K 8/06* | (2006.01) | |

(52) U.S. Cl.
CPC .................. *A61K 8/19* (2013.01); *A61K 8/26* (2013.01); *A61K 8/965* (2013.01); *A61K 8/99* (2013.01); *A61Q 5/02* (2013.01); *A61Q 5/12* (2013.01); *A61Q 17/00* (2013.01); *A61Q 19/007* (2013.01); *A61Q 19/008* (2013.01); *A61Q 19/10* (2013.01)

(58) Field of Classification Search
CPC .......... A61K 8/19; A61K 8/26; A61K 8/0241; A61Q 5/008; A61Q 19/10; A61Q 1/12; A61Q 5/02; A61Q 17/00; A61Q 19/008; A61Q 5/12; A61Q 19/007
See application file for complete search history.

(56) References Cited

U.S. PATENT DOCUMENTS

| | | | | |
|---|---|---|---|---|
| 5,871,754 | A | * | 2/1999 | Briggs .................. A61K 8/362 424/401 |
| 2002/0161104 | A1 | | 10/2002 | Labrousse et al. |
| 2006/0008423 | A1 | | 1/2006 | Araya et al. |
| 2017/0079891 | A1 | | 3/2017 | Joliff et al. |
| 2019/0168145 | A1 | * | 6/2019 | Wang ....................... B01J 20/10 |

FOREIGN PATENT DOCUMENTS

| | | |
|---|---|---|
| CN | 106232089 A | 12/2016 |
| DE | 3147024 A1 | 6/1983 |
| EP | 0200 839 B1 | 12/1989 |
| JP | H09183617 | 7/1997 |
| JP | 2017-036281 A | 2/2017 |
| KR | 2013-0074136 | 7/2013 |
| WO | WO 97/02211 | 1/1997 |
| WO | WO 00/78675 A1 | 12/2000 |
| WO | WO 2010/042614 A1 | 4/2010 |
| WO | WO 2011/012394 A1 | 2/2011 |
| WO | WO 2012/072245 A2 | 6/2012 |
| WO | WO 2013/041274 A1 | 3/2013 |
| WO | WO 2013/190102 A2 | 12/2013 |
| WO | WO 2014/136993 | 6/2014 |
| WO | WO 2014/143728 A1 | 8/2014 |
| WO | WO 2014/140890 A2 | 9/2014 |
| WO | WO 2015/097228 | 7/2015 |
| WO | WO 2016/146708 A1 | 9/2016 |

OTHER PUBLICATIONS

International Search Report and Written Opinion dated Apr. 4, 2018, in International Application No. PCT/EP2018/053947 (15 pgs.).

Bear, J., "The Equation of Motion of a Homogeneous Fluid," Derivations of Darcy's Law in Dynamics of Fluids in Porous Media, $2^{nd}$ Ed. 1988, 161-177.

Gerhardt, L.-C et al., "Fabrication, Characterisation and Tribological Investigation of Artificial Skin Surface Lipid Films," Tribol. Lett (2009) 34:81-93.

Li, Xiang "Anti-aging Cosmetics and Its Efficacy Assessment Methods," 2015 Global Conference on Polymer & Composite Materials, IOP Conf. Series, Minerals Science & Engineering 87, 2015 012043.

Search Report from Application No. 201880012130.3 dated Aug. 2, 2022. (3 pages ).

* cited by examiner

US 11,737,960 B2

USE OF A PARTICULATE MINERAL TO REDUCE POLLUTION

CLAIM FOR PRIORITY

This application is a U.S. national phase entry under 35 U.S.C. § 371 from PCT International Application No. PCT/EP2018/053947, filed Feb. 16, 2018, which claims the benefit of priority of EP Application No, 17305177.2, filed Feb. 17, 2017, from both of which this application claims priority and both of which are incorporated herein by reference.

TECHNICAL FIELD

The present invention generally relates to the use of one or more particulate minerals as anti-pollution agents in compositions suitable for and/or intended for application to the skin and/or keratin materials. The present invention further relates to methods for protecting skin and/or keratin materials from pollution by applying a composition comprising at least one particulate mineral to the skin and/or keratin materials. The present invention also relates to compositions comprising particulate minerals, compositions comprising particulate minerals for use in therapeutic methods and methods for making said compositions.

BACKGROUND

Pollution is known to have a negative impact on the skin and/or keratin materials such hair and nails. For example, pollution may reduce the amount of vitamin E in the skin, reduce respiration of skin cells, increase desquamation, increase sebum secretion and accelerate skin aging and loss of elasticity/firmness. As the population living in cities increases, increasing numbers of individuals are exposed to high levels of pollution and are therefore at risk of the negative effects of pollution. There is therefore an increasing interest from consumers in products that can protect the skin from pollution. There is also an increasing interest in natural, non-chemical products for application to the skin and/or keratin materials. It is therefore desirable to provide improved and/or alternative compositions to protect the skin and/or keratin materials from pollution.

SUMMARY

In accordance with a first aspect of the present invention there is provided the use of a particulate mineral as an anti-pollution agent in a composition for application to the skin and/or keratin materials.

In certain embodiments, the particulate mineral and/or composition absorbs the pollution and/or reduces or prevents entry of pollution into the skin.

In certain embodiments, the particulate mineral and/or composition increases cell respiration and/or reduces desquamation and/or inhibits skin aging and/or reduces loss of skin firmness and/or elasticity and/or reduce secretion of sebum and/or increase vitamin E levels in the skin.

In certain embodiments, the use may be cosmetic. In certain embodiments, the use may be therapeutic. Thus, in a further aspect of the present invention there is provided a composition comprising a particulate mineral for use as an anti-pollution agent in a therapeutic composition.

In accordance with a second aspect of the present invention there is provided a method for protecting skin and/or keratin materials from pollution, wherein the method comprises applying a composition comprising a particulate mineral to the skin and/or keratin materials.

In certain embodiments, the particulate mineral and/or composition absorbs the pollution and/or reduces or prevents entry of pollution into the skin.

In certain embodiments, the particulate mineral and/or composition increases cell respiration and/or reduces desquamation and/or inhibits skin aging and/or reduces loss of skin firmness and/or elasticity and/or reduces secretion of sebum and/or increases vitamin E levels in the skin.

In certain embodiments, the method may be cosmetic. In certain embodiments, the method may be therapeutic. Thus, in a further aspect of the present invention there is provided a composition comprising a particulate mineral for use as an anti-pollution agent in a therapeutic method.

In accordance with a third aspect of the present invention there is provided a composition comprising a particulate mineral. The composition is suitable for and/or intended for application to the skin and/or keratin materials. The particulate mineral is an anti-pollution agent.

In certain embodiments, the composition is a cosmetic composition. In certain embodiments, the composition is a therapeutic composition suitable for and/or intended for a therapeutic use.

In accordance with a fourth aspect of the present invention there is provided a method for making a composition according to any aspect or embodiment described herein. The method may, for example, comprise combining a particulate mineral with a liquid carrier.

Certain embodiments of any aspect of the present invention may provide one or more of the following advantages:
  anti-pollution effect;
    shield from pollution
    absorption of pollution
    prevent/reduce pollution from entering the skin
  increase cell respiration (e.g. skin cell respiration);
  reduce desquamation;
  inhibit skin aging;
  reduce loss of skin firmness and/or elasticity;
  reduce secretion of sebum;
  increase vitamin E levels;
  provides a natural additive.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

Figure 1:
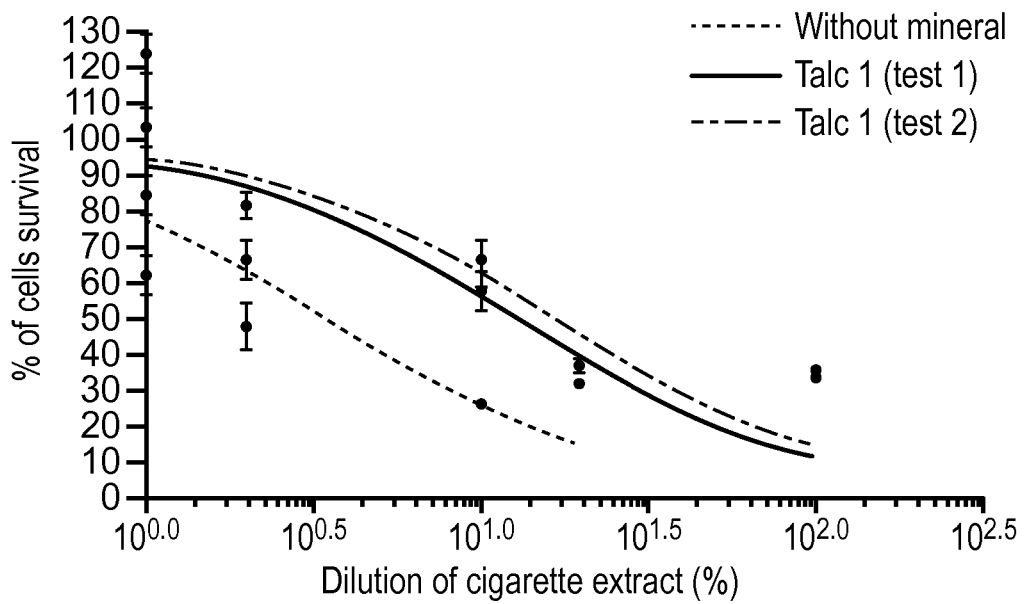
FIG. 1 shows % cell survival vs. cigarette extract dilution (%) when the cigarette extract is filtered through Talc 1 (test repeated twice) in comparison to when the cigarette extract is not filtered through any mineral.

There is provided herein the use of a particulate mineral as an anti-pollution agent in a composition that is suitable for and/or intended for application to the skin and/or keratin materials. There is further provided herein a method for protecting skin and/or keratin materials from pollution, wherein the method comprises applying a composition comprising a particulate mineral to the skin and/or keratin materials.

The term "anti-pollution agent" as used herein means an agent that reduces and/or prevents one or more adverse effects of one or more pollutants on the skin and/or keratin materials. The expression "protecting skin and/or keratin materials from pollution" as used herein means that one or more adverse effects of one or more pollutants on the skin are reduced or prevented. The term "pollutant" as used herein refers to substances that have harmful effects on the skin and includes, for example, air pollutants such as carbon particulates, volatile organic compounds, polycyclic aromatic hydrocarbons, heavy metals (e.g. arsenic, cadmium, chromium, mercury, neodymium, nickel, lead, antimony, bismuth), atmospheric particulate matter including fine particles with a diameter of 10 μm or less ($PM_{10}$), fine particles with a diameter of 2.5 μm or less ($PM_{2.5}$) and ultrafine particles having a diameter of 100 nanometers or less, and toxic gases (e.g. $NO_2$, carbon monoxide, $SO_2$, $O_3$), chemical products (e.g. pesticides), and free radicals. The term "pollutant" does not include UV radiation.

Without wishing to be bound by theory, it is believed that the particulate mineral acts as a shield against pollutants. Thus, in certain embodiments, the particulate mineral absorbs one or more pollutants. In certain embodiments, the particulate mineral reduces or prevents entry of one or more pollutants into the skin. In certain embodiments, the particulate mineral reduces or prevents entry of all pollutants into the skin.

In certain embodiments, the particulate mineral reduces the amount of carbon particles on the skin by at least about 30 wt %. For example, the particulate mineral may reduce the amount of carbon particles on the skin by at least about 35 wt % or at least about 40 wt % or at least about 45 wt % or at least about 50 wt % or at least about 55 wt % or at least about 60 wt % or at least about 65 wt % or at least about 70 wt %. This may, for example, be in comparison to the amount of carbon particles on the skin to which no composition comprising particulate mineral has been applied or in comparison to the amount of carbon particles on the skin to which an identical composition except that it does not comprise the particulate mineral has been applied. This may, for example, be determined by observing the number of carbon particles on the surface of skin using a camera and magnification lens.

In certain embodiments, the particulate mineral and/or composition may have one or more of the following effects:
increase in cell respiration;
reduce or prevent desquamation;
reduce or prevent skin aging;
reduce or prevent loss of skin firmness and/or elasticity;
reduce or prevent secretion of sebum;
increase in vitamin E.

Where one of more of the effects recited above are obtained, the increase or reduction may, for example, be determined in comparison to the skin prior to application of the composition comprising the particulate mineral. Alternatively, the increase or reduction may be determined in comparison to skin on which the composition comprising the particulate mineral has not been applied or on which a composition that is identical except that it does not comprise the particulate mineral has been applied.

Each effect may, for example, be observed by eye or may be measured by methods known to those skilled in the art. The properties of the compositions and pharmaceutical compositions disclosed herein (e.g. anti-pollution effect) may be determined in vivo or in vitro or ex vivo. For example, the effect of pollution on the skin may be measured using skin biopsies, for example by measuring biological markers. For example, cell respiration may be measured by determining the amount of glucose and/or oxygen consumed or by measuring the amount of carbon dioxide produced by the cells. The amount of vitamin E in the skin may, for example, be deduced by measuring the amount of vitamin E in the blood. Skin aging may, for example, be measured by one or more of the methods described in "Anti-aging cosmetics and its efficacy assessment methods", Xiang U, 2015 Global Conference on Polymer and Composite Materials, IOP Conf. Series: Materials Science and Engineering 87 (2015) 012043, the contents of which are incorporated herein by reference. Skin firmness and/or elasticity may, for example, be measured by determining the skin's response to the application of pressure. Sebum secretion may, for example, be measured using a sebumeter.

In certain embodiments, the composition is for topical application. In other words the composition is for application to the skin and/or keratin materials, including, for example, skin, scalp, eyelashes, eyebrows, nails and mucous membranes.

In certain embodiments, the use and/or method is a cosmetic use and/or method and the composition comprising the particulate material is a cosmetic composition.

In certain embodiments, the use or method is respectively a therapeutic use or therapeutic method and the composition comprising the particulate material is a pharmaceutical composition suitable for and/or intended for a therapeutic use/method. The term "pharmaceutical composition" in the context of this invention means a composition comprising (a pharmaceutically effective amount of) particulate mineral and one or more pharmaceutically acceptable carriers and/or excipients and/or diluents.

In certain embodiments, the composition is suitable for and/or intended for application to healthy skin. In certain embodiments, the composition is suitable for and/or intended for application to dry or damaged skin.

In certain embodiments, protection of the skin and/or keratin materials from pollution may, for example, treat or prevent one or more medical conditions. For example, protection of the skin and/or keratin materials from pollution may treat or prevent one or more skin conditions such as atopic dermatitis, lupus, acne, psoriasis, rosacea, eczema, hives and skin cancer.

The expression "treating or preventing" and analogous terms used herein refers to all applications intended to remove or avoid the disorder or to relieve its symptoms, including preventive and curative care, as judged according to any of the tests available according to the prevailing medical practice. An intervention that aims with reasonable expectation to achieve a particular result but does not always do so is included within the expression "treating or preventing". An intervention that succeeds in slowing or halting progression of a disorder is included within the expression "treating or preventing".

The amount of composition administered may be varied depending upon the requirements of the subject. For both therapeutic and non-therapeutic applications, the amount of composition administered may be varied depending upon the desired results, the requirements of the subject and the level of pollution encountered.

Determination of the proper amount/dosage for a particular situation is within the skill of the art. For example, for therapeutic applications a physician or veterinarian having ordinary skill in the art can readily determine and prescribe the effective amount of the pharmaceutical composition required. The total daily amount/dosage may be divided and administered in portions during the day if desired.

In general, a suitable daily dose of active agents in the composition according to the invention will be that amount which is the lowest dose effective to produce the desired effect, for example, a therapeutic effect, and/or to absorb pollution and/or to prevent entry of pollution into the skin. It is contemplated that a wide range of doses may be used, due to the non-toxic nature of the composition. A person of ordinary skill in the art will understand that a suitable dose or dosage will typically vary from subject to subject, and will dependent on factors such as the type of pollution and/or the severity of health conditions of the subject at the outset of administration of the composition. For example, the composition may be administered as two or three or more sub-doses administered separately at appropriate intervals throughout the day, optionally in unit dosage forms.

In certain embodiments, the subject is a human. In other embodiments, the subject is a mammal other than a human, such as non-human primates (e.g. apes, monkeys and lemurs), companion animals such as cats or dogs, working and sporting animals such as dogs, horses and ponies, farm animals such as pigs, sheep, goats, deer, oxen and cattle, and laboratory animals such as rodents (e.g. rabbits, rats, mice, hamsters, gerbils or guinea pigs).

In certain embodiments, the composition is one or more of a hair shampoo, a hair conditioner, a moisturizer (e.g. hand, body and/or foot moisturizer), an eye cream, a cleanser (e.g. a face or body cleanser such as liquid soaps for use in shower and/or bath), a primer, a lip salve, a makeup product (e.g. foundation, concealer, CC cream, BB cream, face or body powder (e.g. pressed or loose powder), bronzer, highlighter, blusher, eyeshadow, mascara, lipstick, highlighter, eyeliner, eyebrow applicator), a hand sanitizer and a hair spray.

In certain embodiments, the composition is a liquid preparation, for example in the form of an, elixir, syrup, suspension, spray, emulsion, lotion, gel, cream and solutions. For example, in certain embodiments the composition is in the form of a gel, cream, lotion or emulsion. Techniques and formulations generally may be found in Remington, The Science and Practice of Pharmacy, Mack Publishing Co., Easton, PA., latest edition.

The composition or pharmaceutical composition may further comprise other biologically active agents. For example, the composition or pharmaceutical composition may further comprise biologically active agents suitable for inhibiting or reducing skin aging or loss of skin firmness and/or elasticity or desquamation, biologically active agents suitable for increasing cell respiration, biologically active agents suitable for reducing or preventing secretion of sebum and/or biologically active agents for increasing vitamin E in the skin. For example, the composition or pharmaceutical composition may further comprise one or more biologically active agents suitable for treating and/or preventing one or more skin conditions such as atopic dermatitis, lupus, acne, psoriasis, rosacea, eczema, hives and skin cancer. For example, the composition or pharmaceutical composition may further comprise one or more vitamins, minerals, skin-replenishing agents, skin-restoring agents, skin-softening agents, skin-soothing agents and sunscreen actives.

The composition may further contain ingredients selected from, for example, absorbents, excipients, diluents, carriers, adjuvants, excipients, vehicles, preserving agents, fillers, hydrating agents, binders, colouring agents, disintegrating agents, wetting agents, emollients, emulsifying agents, suspending agents, sweetening agents, flavouring agents, perfuming agents, antibacterial agents, antifungal agents, antioxidants, cleansing agents, exfoliating agents, lubricating agents, texture enhancing agents, coating agents, encapsulating agents, film-forming agents, thickening agents and dispersing agents, depending on the nature of the mode of administration and dosage forms. One or more (e.g. all) of the further ingredients may, for example, be skin-compatible in that they do not have any adverse effect when applied to the skin and/or keratin materials.

There is also provided herein a method of making a composition suitable for and/or intended for application to skin and/or keratin materials. The composition may, for example, be according to any one or more of the aspects or embodiments disclosed herein.

The method comprises combining the particulate mineral with a liquid carrier. In certain embodiments, the particulate mineral may be combined with a liquid carrier by mixing and/or blending by any technique known to those skilled in the art.

Any particulate mineral suitable for absorbing pollution and/or reducing or preventing entry of pollution into the skin may be used in the present invention.

The particulate mineral may, for example, be used in any effective amount (amount sufficient to achieve the desired aim such as increase in cell respiration, reduction or prevention of desquamation, reduction or prevention skin aging, reduction or prevention of loss of skin firmness and/or elasticity, reduction or prevention of secretion of sebum, or increase in vitamin E. The particulate mineral may, for example, be present in the composition for application to skin and/or keratin materials in an amount ranging from about 0.5 wt % to about 60 wt %. For example, the particulate mineral may be present in the composition in an amount ranging from about 1 wt % to about 55 wt % or from about 1 wt % to about 50 wt % or from about 2 wt % to about 45 wt % or from about 3 wt % to about 40 wt % or from about 4 wt % to about 35 wt % or from about 5 wt % to about 30 wt %.

In certain embodiments, the mineral is a silica-based mineral or a silicate-based mineral. A silica-based mineral is a mineral that comprises greater than 50 wt % silica ($SiO_2$). A silicate-based mineral is a mineral that comprises greater than 50 wt % of a chemical compound that comprises silicate ions (e.g. orthosilicate ions ($SiO_4^{4-}$) or other silicate ions ($[SiO_{2+n}]^{2n-}$)). For example, a silica-based mineral may be a mineral that comprises greater than 60 wt % or greater than 70 wt % or greater than 80 wt % or greater than 90 wt % silica. For example a silicate-based mineral may be a mineral that comprises greater than 60 wt % or greater than 70 wt % or greater than 80 wt % or greater than 90 wt % of a chemical compound that comprises silicate ions.

In certain embodiments, the mineral is naturally-derived (derived from a natural mineral). In certain embodiments, the mineral is synthetic. "Naturally-derived" means that the mineral is either naturally occurring or is made from a naturally occurring mineral. Any mineral that is naturally occurring or made from a naturally occurring mineral is not synthetic. Where the mineral is naturally-derived, it may be that some mineral impurities will inevitably contaminate the ground material. In general, however, the mineral will contain less than 5% by weight, preferably less than 1% by weight of other mineral impurities.

Silica-based minerals include both naturally-derived silica-based minerals and synthetic silica-based minerals. Naturally-derived silica-based minerals include, for example, free silica, natural glasses, diatomaceous earth or mixtures thereof.

Free silica includes, for example, quartz, tridymite, cristobalite, opal, vitreous silica, coesite, stishovite and chalcedony.

Natural glasses (commonly referred to as volcanic glasses) are formed by the rapid cooling of siliceous magma or lava. Several types of natural glasses are known, including, for example, perlite, pumice, pumicite, shirasu, obsidian, and pitchstone. Prior to processing, perite may be gray to green in color with abundant spherical cracks that cause it to break into small pearl-like masses. Pumice is a lightweight glassy vesicular rock. Obsidian may be dark in color with a vitreous luster and a characteristic conchoidal fracture. Pitchstone has a waxy resinous luster and may be brown, green, or gray. Volcanic glasses such as perlite and pumice occur in massive deposits and find wide commercial use. Volcanic ash, often referred to as "tuff" when in consolidated form, includes small particles or fragments that may be in glassy form.

As used herein, the term natural glass encompasses volcanic ash. Natural glasses may be chemically equivalent to rhyolite. Natural glasses that are chemically equivalent to trachyte, dacite, andesite, latite, and basalt are known but may be less common. The term "obsidian" is generally applied to large numbers of natural glasses that are rich in silica. Obsidian glasses may be classified into subcategories according to their silica content, with rhyolitic obsidians (containing typically about 73% $SiO_2$ by weight) being the most common.

Perlite is a hydrated natural glass that may contain, for example, about 72 to about 75% $SiO_2$, about 12 to about 14% $Al_2O_3$, about 0.5 to about 2% $Fe_2O_3$, about 3 to about 5% $Na_2$, about 4 to about 5% $K_2O$, about 0.4 to about 1.5% CaO (by weight), and small amounts of other metallic elements. Perlite may be distinguished from other natural glasses by a higher content (such as about 2 to about 5% by weight) of chemically-bonded water, the presence of a vitreous, pearly luster, and characteristic concentric or arcuate onion skin-like (i.e., perlitic) fractures. Perite may be expanded or non-expanded. Perlite products may be prepared by milling and thermal expansion, and may possess unique physical properties such as high porosity, low bulk density, and chemical inertness. Average particle size for the milled expanded perlite ranges from 5 to 200 microns, pore volume ranges from 2 to 10 L/mg with median pore size from 5 to 20 microns.

Pumice is a natural glass characterized by a mesoporous structure (e.g., having pores or vesicles with a size up to about 1 mm). The porous nature of pumice gives it a very low apparent density, in many cases allowing it to float on the surface of water. Most commercial pumice contains from about 60% to about 70% $SiO_2$ by weight. Pumice may be processed by milling and classification, and products may be used as lightweight aggregates and also as abrasives, adsorbents, and fillers. Unexpanded pumice and thermally-expanded pumice may also be used as filtration components.

Diatomaceous earth products may be obtained from diatomaceous earth (also called "DE" or "diatomite" or "kieselgur"), which is generally known as a sediment-enriched in biogenic silica (i.e., silica produced or brought about by living organisms) in the form of siliceous skeletons (frustules) of diatoms. Diatoms are a diverse array of microscopic, single-celled, golden-brown algae or algae-like plants generally of the class Bacllariophyceae that possess an ornate siliceous skeleton of varied and intricate structures including two valves that, in the living diatom, fit together much like a pill box. Diatomaceous earth may form from the remains of water-borne diatoms and, therefore, diatomaceous earth deposits may be found close to either current or former bodies of water. Those deposits are generally divided into two categories based on source: freshwater and saltwater. Freshwater diatomaceous earth is generally mined from dry lakebeds and may be characterized as having a low crystalline silica content and a high iron content. In contrast, saltwater diatomaceous earth is generally extracted from oceanic areas and may be characterized as having a high crystalline silica content and a low iron content.

Diatomaceous earth is principally composed of the silica microfossils of aquatic unicellular algae known as diatoms. Diatomaceous earth typically has a chemical composition in the range of about 60 to 95% silica, 1 to 12% alumina and 0.5 to 8% iron oxide. It may also contain small amounts of other compounds such as calcium oxide, titanium dioxide, magnesium oxide, sodium oxide and potassium oxide. Diatomaceous earth has a highly porous structure, for example containing up to 80 to 90% voids, and consists of particles of a wide variety of shapes and sizes. In one embodiment, natural diatomaceous earth comprises about 90% $SiO_2$ mixed with other substances. In another embodiment, crude diatomaceous earth comprises about 90% $SiO_2$, plus various metal oxides, such as but not limited to Al, Fe, Ca, and Mg oxides.

The diatomaceous earth starting material may have any of various appropriate forms now known to the skilled artisan or hereafter discovered. In one embodiment, the at least one natural diatomaceous earth is unprocessed (e.g., not subjected to chemical and/or physical modification processes). Without wishing to be bound by theory, the impurities in natural diatomaceous earth, such as clays and organic matters, may, in some embodiments, provide higher cation exchange capacity. The diatomaceous earth may, for example, have an average particle size ranging from about 5 to about 200 microns. The diatomaceous earth may, for example, have a surface area ranging from 1 to 80 $m^2/g$. The diatomaceous earth may, for example have a pore volume ranging from 2 to 10 L/mg with a media pore size from 1 to 20 microns.

Where the mineral is diatomaceous earth, the mineral may have a low cristobalite content. For example, the cristobalite content may be less than about 2% by weight.

For example, the cristobalite content may be less than about 1% by weight. For example, the cristobalite content may be less than about 0.5% by weight. For example, the cristobalite content may be less than about 0.1% by weight. Cristobalite content may be measured by any appropriate measurement technique now known to the skilled artisan or hereafter discovered, including the specific method described in WO 2010/042614, the contents of which are incorporated herein by reference.

Where the mineral is diatomaceous earth, the mineral may comprise at least one metal, for example at least one soluble metal. As used herein, the term "soluble metal" refers to any metal that may be dissolved in at least one liquid. Soluble metals are known to those of skill in the art and include, but are not limited to, iron, aluminium, calcium, vanadium, chromium, copper, zinc, nickel, cadmium, and mercury. When a filter aid comprising diatomaceous earth is used to filter at least one liquid, at least one soluble metal may dissociate from the diatomaceous earth filter aid and enter the liquid. Any appropriate protocol or test for measuring levels of at least one soluble metal in diatomaceous earth products may be used, including those now known to the skilled artisan or hereafter discovered. For example, the brewing industry has developed at least one protocol to measure the BSI of diatomaceous earth filter aids. BSI, or beer soluble iron, refers to the iron content, which may be measured in parts per million, of a filter aid comprising diatomaceous earth that dissociates in the presence of a liquid, such as beer. The European Beverage Convention (EBC) method contacts liquid potassium hydrogen phthalate with the filter aid and then analyzes the liquid for iron content. More specifically, the EBC method uses, for example, a 10 g/L solution of potassium hydrogen phthalate (KHP, $KHC_8H_4O_4$) as the extractant along with a given quantity of filter aid material, with a total contact time of two hours. Extracts are then analyzed for iron concentration by the FERROZINE method. In certain embodiments, the diatomaceous earth comprises equal to or less than about 30 ppm of each soluble metal or total soluble metal. In For example, the diatomaceous earth may comprise equal to or less than about 25 ppm or equal to or less than about 20 ppm or equal to or less than about 20 ppm or equal to or less than about 15 ppm or equal to or less than about 10 ppm or equal to or less than about 5 ppm or equal to or less than about 2 ppm of each soluble metal or total soluble metal. In certain embodiments, the diatomaceous earth independently comprises equal to or less than about 30 ppm of each of arsenic, cadmium, cobalt, chromium, mercury, neodymium, nickel, lead and antimony. For example, the diatomaceous earth may independently comprise equal to or less than about 25 ppm or equal to or less than about 20 ppm or equal to or less than about 20 ppm or equal to or less than about 15 ppm or equal to or less than about 10 ppm or equal to or less than about 5 ppm or equal to or less than about 2 ppm of each of these metals.

Where the mineral is diatomaceous earth, the mineral may have a permeability suitable for use in a filter aid composition. Permeability may be measured by any appropriate measurement technique now known to the skilled artisan or hereafter discovered. Permeability is generally measured in darcy units or darcy, as determined by the permeability of a porous bed 1 cm high and with a 1 $cm^2$ section through which flows a fluid with a viscosity of 1 mPa·s with a flow rate of 1 $cm^3$/sec under an applied pressure differential of 1 atmosphere. The principles for measuring permeability have been previously derived for porous media from Darcy's law (see, for example, J. Bear, "The Equation of Motion of a Homogeneous Fluid: Derivations of Darcy's Law," in Dynamics of Fluids in Porous Media 161-177 (2nd ed. 1988)). An array of devices and methods are in existence that may correlate with permeability. In one exemplary method useful for measuring permeability, a specially constructed device is designed to form a filter cake on a septum from a suspension of filtration media in water; the time required for a specified volume of water to flow through a measured thickness of filter cake of known cross-sectional area is measured. Thus, in an embodiment, the product described herein may have a permeability of at least 1.0 Da, preferably at least 3.0 Da.

Synthetic silica-based minerals include, for example, fumed silica, silica fume, precipitated silica and silica gel. In certain embodiments, the silica-based mineral is not a synthetic silica.

Silicate-based minerals include both naturally-derived silicate-based minerals and synthetic silicate-based minerals. Naturally-derived silicate-based minerals include, for example, orthosilicates (e.g. andalusite, mullite), sorosilicates, cyclosilicates (e.g. bentonite, tourmaline), inosilicate (e.g. ferrolsilite, wollastonite), phyllosilicates (e.g. chrystolite, clays such as halloysite, kaolinite, montmorillonite, vermiculite, talc and pyrophyllite, mica) and tectosilicates (e.g. feldspar). The silicate-based mineral may, for example, be any one or more of these silicates. For example, the silicate-based mineral may be calcium silicate, magnesium silicate or combinations thereof.

Naturally-derived silicate-based minerals also include minerals that are made from a naturally occurring mineral. For example, calcium silicate may be made by reacting calcium oxide with a naturally-occurring silica- or silicate-based mineral. For example, calcium silicate may be made by reacting calcium oxide with diatomaceous earth.

Calcium silicate that is made by reacting calcium oxide with diatomaceous earth may, for example, have a diatom-type mineral structure. The calcium silicate may, for example, have a pore volume equal to or greater than about 5.5 mL/g, for example equal to or greater than about 6.0 mL/g.

In one embodiment, the mineral undergoes minimal processing following mining or extraction. In a further embodiment, the mineral is subjected to at least one physical modification process. The skilled artisan will readily know physical modification processes appropriate for use, which may be now known or hereafter discovered; appropriate physical modification processes include, but are not limited to, milling, drying, and air classifying. In yet another embodiment, the mineral is subjected to at least one chemical modification process. The skilled artisan will readily know chemical modification processes appropriate for use in the present inventions, which may be now known or hereafter discovered; appropriate chemical modification processes include but are not limited to, silanization and calcination.

In one embodiment, the particulate mineral is a carbonate, for example a calcium carbonate (including ground calcium carbonate (GCC) and precipitated calcium carbonate (PCC)).

The present invention may tend to be discussed in terms of naturally-derived silica- or silicate-based minerals. In certain embodiments, the particulate mineral is selected from one or more of talc, perlite, kaolin, diatomaceous earth and combinations thereof. For example, the present invention may tend to be discussed in terms of natural glass (e.g. perlite), diatomaceous earth or naturally-derived calcium silicate. For example, in certain embodiments, the mineral is diatomaceous earth. For example, in certain embodiments, the mineral is perite. In certain embodiments, the perlite may be expanded and classified (e.g. roughly classified) perlite. The expanded and classified (e.g. roughly classified) perlite may, for example, have a $d_{50}$ ranging from about 45 to about 75 µm, for example from about 50 to about 70 µm. In certain embodiments, the perlite may be expanded and milled perite. The expanded and milled perlite may, for example, have a $d_{50}$ ranging from about 20 to about 60 µm, for example from about 30 to about 50 µm. However, the invention should not be construed as being limited to such embodiments.

The composite materials disclosed herein have a particle size. Particle size may be measured by any appropriate measurement technique now known to the skilled artisan or hereafter discovered. Unless otherwise stated, particle size and particle size properties, such as particle size distribution ("psd"), are measured using a Leeds and Northrup Microtrac X100 laser particle size analyzer (Leeds and Northrup, North Wales, Pennsylvania., USA), which can determine particle size distribution over a particle size range from 0.12 µm to 704 µm. The size of a given particle is expressed in terms of the diameter of a sphere of equivalent diameter that sediments through the suspension, also known as an equivalent spherical diameter or "esd." The median particle size, or $d_{50}$ value, is the value at which 50% by weight of the particles have an esd less than that $d_{50}$ value. The $d_{10}$ value is the value at which 10% by weight of the particles have an esd less than that $d_{10}$ value. The $d_{90}$ value is the value at which 90% by weight of the particles have an esd less than that $d_{90}$ value.

The particulate mineral may, for example, have a $d_{10}$ ranging from about 0.05 to about 50 µm. For example, the mineral may have a $d_{10}$ ranging from about 0.1 to about 45 µm, for example from about 0.2 to about 40 µm, for example from about 0.3 to about 35 µm, for example from about 0.4 to about 30 µm, for example from about 0.5 to about 25 µm, for example from about 1 to about 20 µm, for example from about 2 to about 15 µm, for example from about 5 to about 10 µm.

The particulate mineral may, for example, have a $d_{10}$ ranging from about 0.5 to about 100 µm. For example, the mineral may have a $d_{10}$ ranging from about 0.5 to about 98 µm, for example from about 0.5 to about 95, for example from about 0.5 to about 90 µm, for example from about 1 to about 85 µm, for example from about 1 to about 80 µm, for example from about 1 to about 75 µm, for example from about 1 to about 70 µm. For example, the mineral may have a $d_{50}$ ranging from about 2 to about 65 µm, for example from about 2 to about 60 µm, for example from about 2 to about 55 µm. For example, the mineral may have a $d_{50}$ ranging from about 5 to about 50 µm, for example from about 5 to about 45 µm, for example from about 5 to about 40 µm or from about 5 to about 35 µm or from about 5 to about 30 µm or from about 5 to about 25 µm or from about 5 to about 20 µm or from about 5 to about 15 µm or from about 5 to about 10 µm.

The particulate mineral may, for example, have a $d_{90}$ ranging from about 1 to about 200 µm. For example, the mineral may have a $d_{90}$ ranging from about 2 to about 190 µm, for example from about 2 to about 180 µm, for example from about 3 to about 170 µm, for example from about 3 to about 160 µm, for example from about 4 to about 150 µm, for example from about 5 to about 140 µm, for example from about 6 to about 130 µm, for example from about 6 to about 120 µm, for example from about 7 to about 110 µm, for example from about 7 to about 100 µm, for example from about 8 to about 90 µm, for example from about 8 to about 80 µm, for example from about 9 to about 70 µm, for example from about 9 to about 60 µm, for example from about 10 to about 50 µm, for example from about 10 to about 40 µm, for example from about 15 to about 30 µm, for example from about 20 to about 25 µm.

The particulate mineral may, for example, have a lamellarity index of at least about 1. For example, the particulate mineral may have a lamellarity index of at least about 1.5 or at least about 2 or at least about 2.5 or at least about 3. For example, the particulate mineral may have a lamellarity index ranging from about 1 to about 20 or from about 1 to about 15 or from about 1 to about 10 or from about 1 to about 5.

As used herein, the term "lamellarity index" is defined by the following ratio:

$$\frac{d_{50laser} - d_{50sedi}}{d_{50sedi}}$$

in which "$d_{50laser}$" is the value of the mean particle size ($d_{50}$) obtained using a laser particle size analyser as described above and "$d_{50sedi}$" is the value of the median diameter obtained by sedimentation using a sedigraph (standard ISO 13317-3), as described below. Reference may be made to the article by G. Baudet and J. P. Rona, Ind. Min. Mines et Carr. Les techn. June, July 1990, pp 55-61, which shows that this index is correlated to the mean ratio of the largest dimension of the particle to its smallest dimension.

In the sedimentation technique referred to above, particle size properties referred to herein for the talc particulate materials are as measured in a well known manner by sedimentation of the particulate material in a fully dispersed condition in an aqueous medium using a Sedigraph 5100 machine as supplied by Micromeritics Instruments Corporation, Norcross, Ga., USA (www.micromeritics.com), referred to herein as a "Micromeritics Sedigraph 5100 unit", and based on application of Stokes' Law. Such a machine provides measurements and a plot of the cumulative percentage by weight of particles having a size, referred to in the art as the 'equivalent spherical diameter' (e.s.d), less than given e.s.d values. The mean particle size $d_{50sedi}$ is the value determined in this way of the particle e.s.d at which there are 50% by weight of the particles which have an equivalent spherical diameter less than that $d_{50}$ value. The $d_{95sedi}$ value is the value at which 95% by weight of the particles have an esd less than that $d_{95sedi}$ value. Particle size properties may be determined in accordance with ISO 13317-3, or any method equivalent thereto.

The particulate mineral may, for example, have a $d_{50sedi}$ ($d_{50}$ measured by sedigraph as described herein) ranging from about 0.1 μm to about 40 μm. For example, the particulate mineral may have a $d_{50sedi}$ ranging from about 0.2 μm to about 35 μm or from about 0.3 μm to about 30 μm or from about 0.4 μm to about 25 μm or from about 0.5 μm to about 20 μm. For example, the particulate mineral may have a $d_{50sedi}$ ranging from about 0.1 μm to about 15 μm or from about 0.2 μm to about 12 μm or from about 0.5 μm to about 10 μm or from about 0.5 μm to about 8 μm or from about 0.5 μm to about 5 μm.

In certain embodiments, the particulate mineral is talc having a $d_{50}$ ranging from about 1 μm to about 50 μm, for example from about 5 μm to about 40 μm, for example from about 10 μm to about 30 μm, for example from about 10 μm to about 25 μm.

In certain embodiments, the particulate mineral is talc having a $d_{50}$ ranging from about 1 μm to about 20 μm, for example from about 5 μm to about 15 μm, for example from about 6 μm to about 14 μm, for example from about 7 μm to about 13 μm, for example from about 8 μm to about 12 μm, for example from about 9 μm to about 11 μm.

In certain embodiments, the particulate mineral is talc having a $d_{50}$ of at least about 5 μm or at least about 6 μm. For example, the particulate mineral may be talc having a $d_{50}$ of at least about 7 μm or at least about 8 μm or at least about 9 μm or at least about 10 μm. In certain embodiments, the particulate mineral is talc having a $d_{50}$ ranging from about 10 μm to about 50 μm, for example from about 10 μm to about 40 μm, for example from about 10 μm to about 35 μm, for example from about 15 μm to about 35 μm, for example from about 15 μm to about 30 μm or from about 20 μm to about 30 μm or from about 20 μm to about 25 μm or from about 15 μm to about 25 μm or from about 15 μm to about 20 μm.

In certain embodiments, the particulate mineral is talc having a lamellarity index of at least about 1. For example, the particulate mineral may be talc having a lamellarity index of at least about 1.5 or at least about 2 or at least about 2.5. For example, the particulate mineral may be talc having a lamellarity index ranging from about 1 to about 20 or from about 1 to about 15 or from about 1 to about 10 or from about 1 to about 5.

In certain embodiments, the particulate mineral is talc having a $d_{50sedi}$ ($d_{50}$ measured by sedigraph as described herein) of at least about 1 μm. For example, the particulate mineral may be talc having a $d_{50sedi}$ of at least about 1.5 μm or at least about 2 μm or at least about 2.5 μm. For example, the particulate mineral may be talc having a $d_{50sedi}$ ranging from about 1 μm to about 20 μm or from about 1.5 μm to about 15 μm or from about 2 μm to about 12.5 μm or from about 2.5 μm to about 10 μm or from about 2.5 μm to about 7.5 μm or from about 2.5 μm to about 5 μm.

In certain embodiments, the particulate mineral is talc having a $d_{10}$ ranging from about 0.05 μm to about 10 μm, for example from about 0.5 μm to about 9 μm, for example from about 1 μm to about 8 μm, for example from about 2 μm to about 7 μm, for example from about 3 μm to about 6 μm.

In certain embodiments, the particulate mineral is talc having a $d_{90}$ ranging from about 30 μm to about 100 μm, for example from about 30 μm to about 90 μm, for example from about 40 μm to about 80 μm, for example from about 50 μm to about 70 μm, for example from about 55 μm to about 65 μm.

In certain embodiments, the particulate mineral is talc having an aluminium content of less than about 20% based on the total weight of the talc particulate. The aluminium content is calculated as $Al_2O_3$ content, as may be determined by X-ray Fluorescence Spectroscopy (XFS). In certain embodiments, the talc particulate has an aluminium content of less than about 15% by weight, or less than about 10% by weight, or less than about 8.0% by weight, or less than about 6.0% by weight, or less than about 5.0% by weight, or less than about 4.0% by weight, or less than about 3.0% by weight, or less than about 2.0% by weight, or less than about 1.5% by weight, or less than about 1.0% by weight, or less than about 0.75% by weight. In certain embodiments, the talc particulate has an aluminium content of at least about 0.10% by weight, for example, at least about 0.20% by weight, or at least about 0.40% by weight.

In certain embodiments, the particulate mineral is perlite having a $d_{50}$ ranging from about 1 μm to about 40 μm, for example from about 2 μm to about 35 μm, for example from about 5 μm to about 30 μm, for example from about 10 μm to about 25 μm, for example from about 15 μm to about 20 μm. The perlite may, for example, be a milled perlite.

In certain embodiments, the particulate mineral is kaolin having a $d_{50}$ ranging from about 0.5 μm to about 10 μm or from about 0.5 μm to about 9 μm or from about 0.5 μm to about 8 μm or from about 0.75 μm to about 7 μm or from about 0.75 μm to about 6 μm or from about 1 μm to about 5 μm.

In certain embodiments, the particulate mineral is diatomaceous earth having a $d_{50}$ ranging from about 1 μm to about 30 μm, for example from about 2 μm to about 25 μm, for example from about 5 μm to about 20 μm, for example from about 10 μm to about 15 μm. In certain embodiments, the particulate mineral is diatomaceous earth having a $d_{50}$ ranging from about 1 μm to about 20 μm or from about 2 μm to about 15 μm.

In certain embodiments, the mineral is able to absorb substances such as oil and/or sebum and/or water. In certain embodiment, the mineral is able to absorb substances that are in suspension or solution with oil or sebum or water.

In certain embodiments, the mineral has an oil absorption capacity equal to or greater than about 10 mL/100 g of the mineral, for example equal to or greater than about 20 mL/100 g of the mineral. In certain embodiments, the mineral has an oil absorption capacity equal to or greater than about 40 mL/100 g of the mineral. For example, the mineral may have an oil absorption capacity equal to or greater than about 50 mL/100 g of the mineral, for example equal to or greater than about 60 mL/100 g of the mineral, for example equal to or greater than about 70 mL/100 g of the mineral, for example equal to or greater than about 80 mL/100 g of the mineral, for example equal to or greater than about 90 mL/100 g of the mineral, for example equal to or greater than about 100 mL/100 g of the mineral, for example equal to or greater than about 110 mL/100 g of the mineral, for example equal to or greater than about 120 mL/100 g of the mineral, for example equal to or greater than about 130 mL/100 g of the mineral, for example equal to or greater than about 140 mL/100 g of the mineral, for example equal to or greater than about 150 mL/100 g of the mineral, for example equal to or greater than about 160 mL/100 g of the mineral, for example equal to or greater than about 170 mL/100 g of the mineral, for example equal to or greater than about 180 mL/100 g of the mineral, for example equal to or greater than about 190 mL/100 g of the mineral, for example equal to or greater than about 200 mL/100 g of the mineral, for example equal to or greater than about 210 mL/100 g of the mineral.

In certain embodiments, the mineral has a water absorption capacity equal to or greater than about 40 mL/100 g of the mineral. For example, the mineral may have a water absorption capacity equal to or greater than about 50 mL/100 g of the mineral, for example equal to or greater than about 60 mL/100 g of the mineral, for example equal to or greater than about 70 mL/100 g of the mineral, for example equal to or greater than about 80 mL/100 g of the mineral, for example equal to or greater than about 90 mL/100 g of the mineral, for example equal to or greater than about 100 mL/100 g of the mineral, for example equal to or greater than about 110 mL/100 g of the mineral, for example equal to or greater than about 120 mL/100 g of the mineral, for example equal to or greater than about 130 mL/100 g of the mineral, for example equal to or greater than about 140 mL/100 g of the mineral, for example equal to or greater than about 150 mL/100 g of the mineral, for example equal to or greater than about 160 mL/100 g of the mineral, for example equal to or greater than about 170 mL/100 g of the mineral, for example equal to or greater than about 180 mL/100 g of the mineral, for example equal to or greater than about 190 mL/100 g of the mineral, for example equal to or greater than about 200 mL/100 g of the mineral, for example equal to or greater than about 210 mL/100 g of the mineral, for example equal to or greater than about 220 mL/100 g of the mineral, for example equal to or greater than about 230 mL/100 g of the mineral, for example equal to or greater than about 240 mL/100 g of the mineral, for example equal to or greater than about 250 mL/100 g of the mineral, for example equal to or greater than about 260 mL/100 g of the mineral.

In certain embodiments, the mineral has a sebum absorption capacity equal to or greater than about 20 mL/100 g of the mineral, for example equal to or greater than about 30 mL/100 g of the mineral. In certain embodiments, the mineral has a sebum absorption capacity equal to or greater than about 40 mL/100 g of the mineral. For example, the mineral may have a sebum absorption capacity equal to or greater than about 50 mL/100 g of the mineral, for example equal to or greater than about 60 mL/100 g of the mineral, for example equal to or greater than about 70 mL/100 g of the mineral, for example equal to or greater than about 80 mL/100 g of the mineral, for example equal to or greater than about 90 mL/100 g of the mineral, for example equal to or greater than about 100 mL/100 g of the mineral, for example equal to or greater than about 110 mL/100 g of the mineral, for example equal to or greater than about 120 mL/100 g of the mineral, for example equal to or greater than about 130 mL/100 g of the mineral, for example equal to or greater than about 140 mL/100 g of the mineral, for example equal to or greater than about 150 mL/100 g of the mineral, for example equal to or greater than about 160 mL/100 g of the mineral, for example equal to or greater than about 170 mL/100 g of the mineral, for example equal to or greater than about 180 mL/100 g of the mineral, for example equal to or greater than about 190 mL/100 g of the mineral, for example equal to or greater than about 200 mL/100 g of the mineral, for example equal to or greater than about 210 mL/100 g of the mineral, for example equal to or greater than about 220 mL/100 g of the mineral.

In certain embodiments, the mineral may have an oil-absorption capacity ranging from about 10 to about 800 mL/100 g of the mineral. In certain embodiments, the mineral may have an oil-absorption capacity ranging from about 40 to about 800 mL/100 g of the mineral, for example from about 60 to about 750 mL/100 g of the mineral, for example from about 80 to about 700 mL/100 g of the mineral, for example from about 100 to about 650 mL/100 g of the mineral, for example from about 120 to about 600 mL/100 g of the mineral, for example from about 140 to about 550 mL/100 g of the mineral, for example from about 160 to about 500 mL/100 g of the mineral, for example from about 180 to about 450 mL/100 g of the mineral, for example from about 200 to about 400 mL/100 g of the mineral.

In certain embodiments, the mineral may have a water-absorption capacity ranging from about 40 to about 800 mL/100 g of the mineral, for example from about 60 to about 750 mL/100 g of the mineral, for example from about 80 to about 700 mL/100 g of the mineral, for example from about 100 to about 650 mL/100 g of the mineral, for example from about 120 to about 600 mL/100 g of the mineral, for example from about 140 to about 550 mL/100 g of the mineral, for example from about 160 to about 500 mL/100 g of the mineral, for example from about 180 to about 450 mL/100 g of the mineral, for example from about 200 to about 400 mL/100 g of the mineral.

In certain embodiments, the mineral may have a sebum-absorption capacity ranging from about 20 to about 800 mL/100 g of the mineral. In certain embodiments, the mineral may have an sebum-absorption capacity ranging from about 40 to about 800 mL/100 g of the mineral, for example from about 60 to about 750 mL/100 g of the mineral, for example from about 80 to about 700 mL/100 g of the mineral, for example from about 100 to about 650 mL/100 g of the mineral, for example from about 120 to about 600 mL/100 g of the mineral, for example from about 140 to about 550 mL/100 g of the mineral, for example from about 160 to about 500 mL/100 g of the mineral, for example from about 180 to about 450 mL/100 g of the mineral, for example from about 200 to about 400 mL/100 g of the mineral.

In certain embodiments, the particulate mineral is talc having an oil-absorption capacity equal to or greater than about 50 mL/100 g of the mineral. In certain embodiments, the particulate mineral is talc having an oil-absorption capacity ranging from about 10 mL/100 g of the mineral to about 100 mL/100 g of the mineral, for example from about 20 mL/100 g of the mineral to about 100 mL/100 g of the mineral. In certain embodiments, the particulate mineral is talc having an oil-absorption capacity ranging from about 40 mL/100 g of the mineral to about 100 mL/100 g of the mineral. For example, the particulate mineral may be talc having an oil-absorption capacity ranging from about 40 mL/100 g of the mineral to about 90 mL/100 g of the mineral, for example from about 45 mL/100 g of the mineral to about 80 mL/100 g of the mineral, for example from about 50 mL/100 g of the mineral to about 70 mL/100 g of the mineral, for example from about 55 mL/100 g of the mineral to about 60 mL/100 g of the mineral.

In certain embodiments, the particulate mineral is talc having a sebum-absorption capacity equal to or greater than about 60 mL/100 g of the mineral. In certain embodiments, the particulate mineral is talc having a sebum-absorption capacity ranging from about 20 mL/100 g of the mineral to about 100 mL/100 g of the mineral. In certain embodiments, the particulate mineral is talc having a sebum-absorption capacity ranging from about 40 mL/100 g of the mineral to about 100 mL/100 g of the mineral. For example, the particulate mineral may be talc having a sebum-absorption capacity ranging from about 40 mL/100 g of the mineral to about 90 mL/100 g of the mineral, for example from about 45 mL/100 g of the mineral to about 80 mL/100 g of the mineral, for example from about 50 mL/100 g of the mineral to about 70 mL/100 g of the mineral, for example from about 55 mL/100 g of the mineral to about 60 mL/100 g of the mineral.

In certain embodiments, the particulate mineral is talc having a water-absorption capacity ranging from about 40 mL/100 g of the mineral to about 100 mL/100 g of the mineral. For example, the particulate mineral may be talc having a water-absorption capacity ranging from about 40 mL/100 g of the mineral to about 90 mL/100 g of the mineral, for example from about 45 mL/100 g of the mineral to about 80 mL/100 g of the mineral, for example from about 50 mL/100 g of the mineral to about 70 mL/100 g of the mineral, for example from about 55 mL/100 g of the mineral to about 60 mL/100 g of the mineral.

In certain embodiments, the particulate mineral is perlite having an oil absorption capacity equal to or greater than about 120 mL/100 g of the mineral. In certain embodiments, the particulate mineral is perlite having an oil absorption capacity ranging from about 40 mL/100 g of the mineral to about 300 mL/100 g of the mineral, for example from about 50 mL/100 g of the mineral to about 300 mL/100 g of the mineral. In certain embodiments, the particulate mineral is perlite having an oil absorption capacity ranging from about 100 mL/100 g of the mineral to about 200 mL/100 g of the mineral. For example, the particulate mineral may be perlite having an oil absorption capacity ranging from about 110 mL/100 g of the mineral to about 190 mL/100 g of the mineral, for example from about 120 mL/100 g of the mineral to about 180 mL/100 g of the mineral, for example from about 130 mL/100 g of the mineral to about 170 mL/100 g of the mineral, for example from about 140 mL/100 g of the mineral to about 160 mL/100 g of the mineral.

In certain embodiments, the particulate mineral is perlite having a sebum absorption capacity equal to or greater than about 140 mL/100 g of the mineral. In certain embodiments, the particulate mineral is perlite having a sebum absorption capacity ranging from about 50 mL/100 g of the mineral to about 400 mL/100 g of the mineral, for example from about 60 mL/100 g of the mineral to about 350 mL/100 g of the mineral. In certain embodiments, the particulate mineral is perlite having a sebum absorption capacity ranging from about 100 mL/100 g of the mineral to about 200 mL/100 g of the mineral. For example, the particulate mineral may be perlite having a sebum absorption capacity ranging from about 110 mL/100 g of the mineral to about 190 mL/100 g of the mineral, for example from about 120 mL/100 g of the mineral to about 180 mL/100 g of the mineral, for example from about 130 mL/100 g of the mineral to about 170 mL/100 g of the mineral, for example from about 140 mL/100 g of the mineral to about 160 mL/100 g of the mineral.

In certain embodiments, the particulate mineral is perlite having a water absorption capacity ranging from about 150 mL/100 g of the mineral to about 300 mL/100 g of the mineral. For example, the particulate mineral may be perlite having a water absorption capacity ranging from about 180 mL/100 g of the mineral to about 300 mL/100 g of the mineral, for example from about 200 mL/100 g of the mineral to about 300 mL/100 g of the mineral, for example from about 210 mL/100 g of the mineral to about 290 mL/100 g of the mineral, for example from about 220 mL/100 g of the mineral to about 280 mL/100 g of the mineral, for example from about 230 mL/100 g of the mineral to about 270 mL/100 g of the mineral, for example from about 240 mL/100 g of the mineral to about 260 mL/100 g of the mineral.

In certain embodiments, the particulate mineral is kaolin having an oil absorption capacity equal to or greater than about 50 mL/100 g of the mineral. In certain embodiments, the particulate mineral is kaolin having an oil absorption capacity ranging from about 20 mL/100 g of the mineral to about 100 mL/100 g of the mineral, for example from about 30 mL/100 g of the mineral to about 100 mL/100 g of the mineral. In certain embodiments, the particulate mineral is kaolin having an oil absorption capacity ranging from about 40 mL/100 g of the mineral to about 100 mL/100 g of the mineral. For example, the particulate mineral may be kaolin having an oil-absorption capacity ranging from about 40 mL/100 g of the mineral to about 90 mL/100 g of the mineral, for example from about 45 mL/100 g of the mineral to about 80 mL/100 g of the mineral, for example from about 50 mL/100 g of the mineral to about 70 mL/100 g of the mineral, for example from about 50 mL/100 g of the mineral to about 60 mL/100 g of the mineral.

In certain embodiments, the particulate mineral is kaolin having a water absorption capacity ranging from about 40 mL/100 g of the mineral to about 100 mL/100 g of the mineral. For example, the particulate mineral may be kaolin having a water absorption capacity ranging from about 40 mL/100 g of the mineral to about 90 mL/100 g of the mineral, for example from about 45 mL/100 g of the mineral to about 80 mL/100 g of the mineral, for example from about 45 mL/100 g of the mineral to about 70 mL/100 g of the mineral, for example from about 50 mL/100 g of the mineral to about 60 mL/100 g of the mineral.

In certain embodiments, the particulate mineral is kaolin having a sebum absorption capacity equal to or greater than about 60 mL/100 g of the mineral. In certain embodiments, the particulate mineral is kaolin having a sebum absorption capacity ranging from about 30 mL/100 g of the mineral to about 120 mL/100 g of the mineral, for example from about 40 mL/100 g of the mineral to about 100 mL/100 g of the mineral. In certain embodiments, the particulate mineral is kaolin having a sebum absorption capacity ranging from about 40 mL/100 g of the mineral to about 150 mL/100 g of the mineral. For example, the particulate mineral may be kaolin having a sebum absorption capacity ranging from about 45 mL/100 g of the mineral to about 120 mL/100 g of the mineral, for example from about 50 mL/100 g of the mineral to about 100 mL/100 g of the mineral, for example from about 60 mL/100 g of the mineral to about 90 mL/100 g of the mineral, for example from about 70 mL/100 g of the mineral to about 80 mL/100 g of the mineral.

In certain embodiments, the particulate mineral is diatomaceous earth having an oil absorption capacity equal to or greater than about 100 mL/100 g, for example equal to or greater than about 120 mL/100 g of the mineral. In certain embodiments, the particulate mineral is diatomaceous earth having an oil absorption capacity ranging from about 40 mL/100 g of the mineral to about 300 mL/100 g of the mineral, for example from about 40 mL/100 g of the mineral to about 300 mL/100 g of the mineral. In certain embodiments, the particulate mineral is diatomaceous earth having an oil absorption capacity ranging from about 70 mL/100 g of the mineral to about 300 mL/100 g of the mineral. For example, the particulate mineral may be diatomaceous earth having an oil absorption capacity ranging from about 75 mL/100 g of the mineral to about 100 mL/100 g of the mineral. For example, the particulate mineral may be diatomaceous earth having an oil absorption capacity ranging from about 150 mL/100 g of the mineral to about 300 mL/100 g of the mineral, for example from about 150 mL/100 g of the mineral to about 250 mL/100 g of the mineral, for example from about 160 mL/100 g of the mineral to about 240 mL/100 g of the mineral, for example from about 170 mL/100 g of the mineral to about 230 mL/100 g of the mineral, for example from about 180 mL/100 g of the mineral to about 220 mL/100 g of the mineral.

In certain embodiments, the particulate mineral is diatomaceous earth having a sebum absorption capacity equal to or greater than about 140 mL/100 g of the mineral. In certain embodiments, the particulate mineral is diatomaceous earth having a sebum absorption capacity ranging from about 50 mL/100 g of the mineral to about 320 mL/100 g of the mineral, for example from about 60 mL/100 g of the mineral to about 310 mL/100 g of the mineral. In certain embodiments, the particulate mineral is diatomaceous earth having a sebum absorption capacity ranging from about 70 mL/100 g of the mineral to about 300 mL/100 g of the mineral. For example, the particulate mineral may be diatomaceous earth having a sebum absorption capacity ranging from about 75 mL/100 g of the mineral to about 100 mL/100 g of the mineral. For example, the particulate mineral may be diatomaceous earth having a sebum absorption capacity ranging from about 150 mL/100 g of the mineral to about 300 mL/100 g of the mineral, for example from about 150 mL/100 g of the mineral to about 250 mL/100 g of the mineral, for example from about 160 mL/100 g of the mineral to about 240 mL/100 g of the mineral, for example from about 170 mL/100 g of the mineral to about 230 mL/100 g of the mineral, for example from about 180 mL/100 g of the mineral to about 220 mL/100 g of the mineral.

In certain embodiments, the particulate mineral is diatomaceous earth having a water absorption capacity ranging from about 70 mL/100 g of the mineral to about 300 mL/100 g of the mineral. For example, the particulate mineral may be diatomaceous earth having a water absorption capacity ranging from about 75 mL/100 g of the mineral to about 120 mL/100 g of the mineral, for example from about 80 mL/100 g of the mineral to about 110 mL/100 g of the mineral. For example, the particulate mineral may be diatomaceous earth having a water absorption capacity ranging from about 150 mL/100 g of the mineral to about 300 mL/100 g of the mineral, for example from about 200 mL/100 g of the mineral to about 300 mL/100 g of the mineral, for example from about 210 mL/100 g of the mineral to about 290 mL/100 g of the mineral, for example from about 220 mL/100 g of the mineral to about 280 mL/100 g of the mineral, for example from about 230 mL/100 g of the mineral to about 280 mL/100 g of the mineral, for example from about 240 mL/100 g of the mineral to about 280 mL/100 g of the mineral, for example from about 250 mL/100 g of the mineral to about 280 mL/100 g of the mineral.

In certain embodiments, the particulate mineral is calcium carbonate (e.g. PCC) having an oil absorption capacity equal to or greater than about 80 mL/100 g, for example equal to or greater than about 100 mL/100 g of the mineral. In certain embodiments, the particulate mineral is calcium carbonate (e.g. PCC) having an oil absorption capacity ranging from about 30 mL/100 g of the mineral to about 150 mL/100 g of the mineral, for example from about 40 mL/100 g of the mineral to about 130 mL/100 g of the mineral. In certain embodiments, the particulate mineral is calcium carbonate (e.g. PCC) having an oil absorption capacity ranging from about 50 mL/100 g of the mineral to about 100 mL/100 g of the mineral. For example, the particulate mineral may be calcium carbonate (e.g. PCC) having an oil absorption capacity ranging from about 75 mL/100 g of the mineral to about 100 mL/100 g of the mineral.

In certain embodiments, the particulate mineral is calcium carbonate (e.g. PCC) having a sebum absorption capacity equal to or greater than about 90 mL/100 g of the mineral. In certain embodiments, the particulate mineral is calcium carbonate (e.g. PCC) having a sebum absorption capacity ranging from about 40 mL/100 g of the mineral to about 150 mL/100 g of the mineral, for example from about 50 mL/100 g of the mineral to about 140 mL/100 g of the mineral. In certain embodiments, the particulate mineral is calcium carbonate (e.g. PCC) having a sebum absorption capacity ranging from about 60 mL/100 g of the mineral to about 130 mL/100 g of the mineral. For example, the particulate mineral may be calcium carbonate (e.g. PCC) having a sebum absorption capacity ranging from about 70 mL/100 g of the mineral to about 120 mL/100 g of the mineral. For example, the particulate mineral may be calcium carbonate (e.g. PCC) having a sebum absorption capacity ranging from about 80 mL/100 g of the mineral to about 110 mL/100 g of the mineral.

In certain embodiments, the particulate mineral is calcium silicate (e.g. synthetic calcium silicate) having an oil absorption capacity equal to or greater than about 280 mL/100 g, for example equal to or greater than about 300 mL/100 g of the mineral. In certain embodiments, the particulate mineral is calcium silicate (e.g. synthetic calcium silicate) having an oil absorption capacity ranging from about 200 mL/100 g of the mineral to about 500 mL/100 g of the mineral, for example from about 250 mL/100 g of the mineral to about 450 mL/100 g of the mineral. In certain embodiments, the particulate mineral is calcium silicate (e.g. synthetic calcium silicate) having an oil absorption capacity ranging from about 300 mL/100 g of the mineral to about 400 mL/100 g of the mineral. For example, the particulate mineral may be calcium silicate (e.g. synthetic calcium silicate) having an oil absorption capacity ranging from about 250 mL/100 g of the mineral to about 350 mL/100 g of the mineral.

In certain embodiments, the particulate mineral is calcium silicate (e.g. synthetic calcium silicate) having a sebum absorption capacity equal to or greater than about 280 mL/100 g, for example equal to or greater than about 300 mL/100 g of the mineral. In certain embodiments, the particulate mineral is calcium silicate (e.g. synthetic calcium silicate) having a sebum absorption capacity ranging from about 200 mL/100 g of the mineral to about 500 mL/100 g of the mineral, for example from about 250 mL/100 g of the mineral to about 450 mL/100 g of the mineral. In certain embodiments, the particulate mineral is calcium silicate (e.g. synthetic calcium silicate) having a sebum absorption capacity ranging from about 300 mL/100 g of the mineral to about 400 mL/100 g of the mineral. For example, the particulate mineral may be calcium silicate (e.g. synthetic calcium silicate) having a sebum absorption capacity ranging from about 250 mL/100 g of the mineral to about 350 mL/100 g of the mineral.

The sebum-absorption capacity, oil-absorption capacity and water-absorption capacities are determined by weighing a sample of mineral into a container (e.g. 1 to 10 grams into a 100 to 300 mL ceramic or glass dish) and adding either sebum, oil or water to the mineral gradually in a dropwise manner (e.g. about 1 drop per second). The sample is stirred during the addition of the liquid so that each drop falls on a dry portion of the mineral sample. When the sample particles become wet with water, they coalesce and form small lumps of paste. These lumps should be kept distributed throughout the mass, using a minimum of stirring, and using care not to use pressure in the mixing. As the absorption of liquid progresses, the lumps of paste form larger lumps which, when stirred around, form balls. When this point is reached, the rate and quantity of the liquid added should be decreased to ensure you do not go past the end point. When adding liquid at this point it should strike the balls, not the dry sample. These balls are stirred around to bring the watery surface into contact with the remaining dry sample. When the dry sample is wet and picked up, the paste lumps tend to smear on the sides and bottom of the casserole. This is the end point. The total amount of water used in noted and the mL of liquid (sebum/oil/water) per 100 g of mineral sample is calculated. The oil may, for example, be linseed oil. The sebum may, for example, be an artificial sebum, for example an artificial sebum as described in Gerhardt L., Fabrication, Characterisation and Tribological Investigation of Artificial Skin Surface Lipid Films. Tribol let. 2009, 34, 81-93.

The oil absorption of the samples may be determined on a weight basis according to ASTM-D1483-95. The oil absorption in weight percentage may be calculated as follows:

$$\text{Oil Absorption (wt. \%)} = \frac{\text{Volume Oil Used (mL)} \times \text{Specific Gravity of Oil}}{\text{Weight of Sample (g)}} \times 100$$

In certain embodiments, the particulate mineral is the form of a free-flowing granulate before it is incorporated into the composition suitable for and/or intended for application to skin and/or keratin materials. "Free-flowing" means that the mineral can move freely, for example the mineral can move in a continuous stream (e.g. "poured"). "Granulate" means that the mineral is in the form of particles or grains (particles formed from more than one smaller particles).

Whether a mineral is in the form of a "free-flowing granulate" may be determined by its base flow energy (BFE). For example, a mineral may be considered to be a "free-flowing granulate" if it has a BFE equal to or less than about 1200 mJ. For example, a mineral may be considered to be "free-flowing" if it has a BFE equal to or less than about 1100 mJ, for example equal to or less than about 1000 mJ, for example equal to or less than about 800 mJ, for example equal to or less than about 700 mJ, for example equal to or less than about 600 mJ.

In certain embodiments, the mineral is in the form of a free-flowing granulate even at relatively high oil and/or water contents. For example, the mineral may be in the form of a free-flowing granulate at a liquid (e.g. organic acid and/or oil and/or water) content of at least about 140 g/100 g of the mineral. For example, the mineral may be in the form of a free-flowing granulate at a liquid content of at least about 150 g/100 g of the mineral, for example at least about 160 g/100 g of the mineral, for example at least about 170 g/100 g of the mineral, for example at least about 180 g/100 g of the mineral, for example at least about 190 g/100 g of the mineral, for example at least about 200 g/100 g of the mineral, for example at least about 210 g/100 g of the mineral, for example at least about 220 g/100 g of the mineral, for example at least about 230 g/100 g of the mineral, for example at least about 240 g/100 g of the mineral, for example at least about 250 g/100 g of the mineral, for example at least about 260 g/100 g of the mineral, for example at least about 270 g/100 g of the mineral, for example at least about 280 g/100 g of the mineral, for example at least about 290 g/100 g of the mineral, for example at least about 300 g/100 g of the mineral. For example, the mineral may be in the form of a free-flowing granulate at a liquid content ranging from about 140 to about 600 g/100 g of the mineral, for example from about 150 to about 550 g/100 g of the mineral, for example from about 160 to about 500 g/100 g of the mineral.

In certain embodiments, the mineral has a base flow energy (BFE) equal to or less that is equal to or less than about 1200 mJ when the mineral has a liquid content of 200 g/100 g of the mineral. For example, the mineral may have a BFE equal to or less than about 1100 mJ when the mineral has a liquid content of 200 g/100 g of the mineral, for example equal to or less than about 1000 mJ when the mineral has a liquid content of 200 g/100 g of the mineral, for example equal to or less than about 900 mJ when the mineral has a liquid content of 200 g/100 g of the mineral, for example equal to or less than about 800 mJ when the mineral has a liquid content of 200 g/100 g of the mineral. For example, the mineral may have a BFE ranging from about 200 to about 1200 mJ when the mineral has a liquid content of 200 g/100 g of the mineral, for example from about 300 to about 1100 mJ when the mineral has a liquid content of 200 g/100 g of the mineral, for example from about 400 to about 1000 mJ when the mineral has a liquid content of 200 g/100 g of the mineral, for example from about 400 to about 800 mJ when the mineral has a liquid content of 200 g/100 g of the mineral.

In certain embodiments, the mineral has a base flow energy (BFE) that is equal to or less than about 1200 mJ when the mineral has a water content of 150 g/100 g of the mineral. For example, the mineral may have a BFE equal to or less than about 1100 mJ when the mineral has a water content of 150 g/100 g of the mineral, for example equal to or less than about 1000 mJ when the mineral has a water content of 150 g/100 g of the mineral, for example equal to or less than about 900 mJ when the mineral has a water content of 150 g/100 g of the mineral, for example equal to or less than about 800 mJ when the mineral has a water content of 150 g/100 g of the mineral. For example, the mineral may have a BFE ranging from about 200 to about 1200 mJ when the mineral has a water content of 150 g/100 g of the mineral, for example from about 300 to about 1100 mJ when the mineral has a water content of 150 g/100 g of the mineral, for example from about 400 to about 1000 mJ when the mineral has a water content of 150 g/100 g of the mineral, for example from about 400 to about 800 mJ when the mineral has a water content of 150 g/100 g of the mineral.

Base flow energy is measured using a Freeman Powder Rheometer model FT3. The FT3 rheometer drives a blade along a helical path downward through a powder sample. As the blade forces it way down through the powder the force imposed upon it is measured. It is this data that forms the basis of the measurements made. The helical path that the blade takes through the sample is determined by a combination of the rotational and axial speeds. Each particle within the powder mass lies at a state of rest until forced to move, coming to rest again as the blade moves on. The pattern of powder displacement is virtually steady state, allowing flow to be observed and generally resulting in smooth, linear or logarithmic profiles of the measured forces. These forces are those required to initiate shearing and breakdown of interparticulate bonding of the powder in the zone immediately around the blade, a process that is continuous.

The base flow energy is the energy required to displace a constant volume of conditioned powder at a given flow pattern and flow rate. Samples are prepared by measuring 160 ml of powder into the sample vessel and recording the mass. A conditioning cycle is then carried out on the sample and the volume rechecked and adjusted to 160 ml if necessary before conducting the test. The BFE test consists of a standard conditioning cycle with blade tip speed of 100 mm/s in a 5° C. negative upward helical path followed by a test cycle with a downward transverse tip speed set at 100 mm/s and a 10° negative helix.

The specific pore volume of a packed body of the granular material may, for example, be at least about 3 cc/g, or at least about 4 cc/g or at least about 5 cc/g. Typically, products of the invention have little, if any, pore volume in pores smaller than 0.1 µm or larger than 100 µm. The majority of the pore volume, for example at least 70% of the pore volume may be in pores larger than 1 µm and smaller than 100 µm. At least 40% of the pore volume may be in pores larger than 10 µm and smaller than 100 µm. Pore volume may be measured by mercury porosimetry using a CE Instruments Model "Pascal 240" mercury porosimeter. The method involves evacuation of the sample placed in a dilatometer, which is subsequently filled with mercury. Pressure is applied to the filled dilatometer and the mercury intrudes first into the intra-particle pores between granules and the hollow voids of the particles, and then into the pores of the granules within the sample under test. The volume of mercury intruded is determined by a precision capacitive electrode and the pore diameter calculated from the applied pressure according to the Washburn equation. The contact angle for porosimetery was 140°, and the pressure typically 0.012 MPa to 200 MPa. The average pore diameter of a packed body of the granular material may be of the order of 5-15 µm, for example about 10 µm. Typically, the average pore diameter of the granules (excluding intra-particle pores and the hollow void formed with the granules) is of the order of 1-3 µm, for example about 2 µm. The mineral may, for example, particularly have a pore volume as described where the mineral is diatomaceous earth.

In certain embodiments, the particulate mineral has a surface area equal to or greater than about 1 m$^2$/g. For example, the mineral may have a surface area equal to or greater than about 2 m$^2$/g or equal to or greater than about 5 m$^2$/g or equal to or greater than about 10 m$^2$/g or equal to or greater than about 20 m$^2$/g or equal to or greater than about 30 m$^2$/g or equal to or greater than about 40 m$^2$/g or equal to or greater than about 50 m$^2$/g or equal to or greater than about 60 m$^2$/g or equal to or greater than about 70 m$^2$/g. For example, the mineral may have a surface area ranging from about 1 m$^2$/g to about 100 m$^2$/g or from about 2 m$^2$/g to about 90 m$^2$/g or from about 5 m$^2$/g to about 80 m$^2$/g.

The surface area of the samples may be determined according to the BET method by the quantity of nitrogen adsorbed on the surface of said particles so to as to form a monomolecular layer completely covering said surface (measurement according to the BET method, AFNOR standard X11-621 and 622 or ISO 9277). In certain embodiments, specific surface is determined in accordance with ISO 9277, or any method equivalent thereto.

In certain embodiments, the particulate mineral has a L whiteness value equal to or greater than about 80. For example, the particulate mineral may have a L whiteness value equal to or greater than about 82 or equal to or greater than about 84 or equal to or greater than about 85 or equal to or greater than about 86 or equal to or greater than about 88 or equal to or greater than about 90 or equal to or greater than about 92 or equal to or greater than about 94. For example, the particulate mineral may have a L whiteness value ranging from about 80 to about 100 or from about 82 to about 98 or from about 84 to about 96 or from about 85 to about 95.

L, a and b may be determined using the Hunter scale collected on a Spectro/plus Spectrophotometer (Colour and Appearance Technology, Inc., Princeton, N.J.) as described in the Examples below.

In certain embodiments, the particulate mineral may be spray-dried (i.e. the product of a spray-drying process). The spray-dried mineral product may, for example, be treated by one or more physical or chemical modification processes, such as milling, drying, air classifying, silanization and calcinations.

The spray-dried mineral may, for example, comprise substantially spherical granules. For example, greater than about 50 wt % of the spray-dried mineral, for example greater than about 60 wt %, for example greater than about 70 wt %, for example greater than about 80 wt %, for example greater than about 90 wt % of the spray-dried mineral may comprise substantially spherical granules. For example, each substantially spherical granule may have a mineral shell surrounded by a hollow core. The product may, for example, have substantially the same form after any of the physical or chemical modification processes described above, for example after calcinations.

The spray-dried mineral may, for example, further comprise a binder, which may, for example, have been included in the suspension that was spray-dried to facilitate the formation of spray-dried granules. A binder that remains associated with or in the product may be referred to as a "permanent binder". Examples of permanent binders are cross-linked alginates, thermosetting resins, thermoplastic resins and styrene-butadiene polymers. The binder may, for example, be present in the spray-dried mineral in an amount equal to or less than about 10 wt %, for example equal to or less than about 8 wt %, for example equal to or less than about 6 wt %, for example equal to or less than about 5 wt %, for example equal to or less than about 4 wt %, for example equal to or less than about 3 wt %, for example equal to or less than about 2 wt %, for example equal to or less than about 1 wt %.

The spray-drying process may yield uniform, or substantially uniform, spray-dried granules, in which case the diameter of the granules will lie in the aforesaid range. The steepness of the particle size distribution curve, as characterized by the $d_{90}/d_{10}$ ratio, is typically at least 5, preferably at least 8. In some embodiments, the spray-dried granulate may be essentially mono-disperse. In certain embodiments, spray-drying a mineral may improve the oil and/or water-absorption properties of the mineral.

Spray-drying is a method of producing a dry powder from a liquid or slurry by rapidly drying using a hot gas. The methods described herein may comprise a step in which a suspension comprising particles of mineral is spray-dried. A mineral granulate is recovered. The recovered granulate may be heat treated (also referred to herein as "calcined").

For example, the methods described herein may comprising spray-drying a suspension comprising particles of a mineral (e.g. a mineral as described herein), a liquid medium and a binder and recovering a spray-dried mineral granulate. The mineral starting material and/or the spray-dried mineral granulate may have any one or more of the characteristics described herein. For example, the spray-dried mineral granulate may have an increased sebum- and/or oil- and/or water-absorption capacity in comparison to the sebum- and/or oil- and/or water-absorption capacity of the mineral prior to the spray-drying step.

The suspension which is to be spray-dried is typically an aqueous suspension comprising a liquid medium and a solids portion. The liquid medium is typically water.

The suspension may further include a binder. The binder may be inorganic or organic and may comprise a solid component, as for example a latex type binder. The binder may be included in the suspension to facilitate the formation of spray-dried granules.

In an embodiment, the binder may be a temporary binder. By "temporary binder" is meant a binder which is not intended to remain in the product but acts to bind particles of the mineral together and support the spray-dried body after initial formation, which can then be subjected to one or more further treatment steps, including steps intended to impart structural rigidity to the spray-dried bodies, such as a heat treatment. Such temporary binders may thus be thermally fugitive, that is to say are removed from the spray-dried bodies on the application of sufficient heat which may vaporize or burn the binder material. Examples of suitable temporary binders are starches, carbohydrates, sugars, poly-vinyl acetates, poly-vinyl alcohols, latex, gelatines, waxes, celluloses, dextrines, thermo-plastic resins, thermo-setting resins, chlorinated hydrocarbons, gums, flours, caseins, alginates, proteins, bitumens, acrylics, epoxy resins, and urea. In embodiments of the invention, the temporary binder may be a poly vinyl alcohol binder or a latex binder. The amount of temporary binder in the suspension may be in the range of up to 10 wt % on a solids basis, for example 2-10 wt %. Where the binder is a temporary binder, the spray-dried granulate may be subjected to a heat treatment, or calcination, step in order to impart structural rigidity to the spray-dried bodies. In the heat treatment step, the temporary binder is removed, or substantially removed, from the spray-dried bodies.

In another embodiment, the binder may be a permanent binder. By "permanent binder" is meant a binder which is intended to remain in the product and provide structural strength to the spray-dried bodies without the need for a high temperature calcination step. Examples of permanent binders are cross-linked alginates, thermosetting resins, thermoplastic resins and styrene-butadiene polymers. The specific permanent binder to be used may be selected to ensure that the binder provides structural support to the aggregate without being significantly soluble in the liquid to be filtered. For example a binder which is insoluble in water would be suitable for use in a filter medium which is to be used in beer filtration.

The permanent binder may also, for example, be cross-linkable. In case such cross-linkable binders are used, a further chemical or low temperature heat treatment (for example less than 200° C.) may be required after the spray-dried bodies are formed in order to effect cross-linking. An example of a suitable cross-linkable binder is a copolymer of a vinyl acetate and an acrylic ester, such as Vinnapas AN214 from Wacker Chemie. It is to be appreciated that permanent binders used in the present invention may be thermally fugitive, if organic in nature. However, a distinction between a temporary binder and a permanent binder which is thermally fugitive is that a permanent binder is capable of fixing the aggregated structure produced during the spray-drying step, without the need for a calcination treatment.

Other permanent binders which are not thermally fugitive may be used. Such binders are inorganic-based. Examples include cements, pozzolanic materials, silcates, waterglass, gypsums, bentonites, and borates. Also included are aluminate binders, including alkali metal aluminate binders such as sodium aluminate, potassium aluminate or lithium aluminate, and alkaline earth metal aluminate binders, such as calcium aluminate and magnesium aluminate. An advantage of using a permanent binder is that a calcination step can be avoided.

The solids portion of the suspension comprises the particulate mineral component together with one or more optional additional inorganic components and one or more optional organic solid components.

The inorganic solids content of the suspension is dependent on the spray-drying method to be used, which is discussed in more detail below, and the size of spray-dried granules desired. Typically, however, in order to have a viscosity suitable for spray-drying, the suspension should have an inorganic solids content of at least 5%, for example at least 10%, for example at least 15% by weight, based on the weight of the suspension, and may have an inorganic solids content of up to 30%, or 25% or 20%, based on the weight of the suspension. Typically, the solids content will be in the range of 15-25% by weight, based on the weight of the suspension.

The optional inorganic component may comprise one or more particulate inorganic mineral in addition to the mineral as described herein; and/or one or more suitable fluxing agent. The optional organic solids component may be the solids component of an organic binder.

A small amount of an additional inorganic mineral component, for example 20% or less, based on the total weight of the inorganic solids in the suspension, for example 10% or less or 5% or less, based on the total weight of the inorganic solids present in the suspension may be included in the suspension that is spray-dried. This will result in spray-dried granules including the additional inorganic mineral component, for example in the outer wall thereof. This may be used to adjust the properties of the spray-dried granules, for example strength and/or permeability.

A fluxing agent is an optional additional component of the suspension that is spray-dried. A fluxing agent may be necessary where the spray-dried granules are to be calcined (so-called "flux-calcining"). The presence of at least one fluxing agent during calcination may reduce the temperature at which mineral particles in the wall of the spray-dried bodies are caused to be sintered together.

Suitable agents as the fluxing agent are any now known to those skilled in the art or which may hereafter be discovered. In one embodiment, the fluxing agent is sodium carbonate (soda ash, $Na_2CO_3$). In another embodiment, the fluxing agent is sodium hydroxide (NaOH). In a further embodiment, the at least one fluxing agent is sodium chloride (NaCl). In yet another embodiment, the at least one fluxing agent is potassium carbonate ($K_2CO_3$). In yet a further embodiment, the at least one fluxing agent is sodium borate ($Na_2B_4O_7$).

In one embodiment, the fluxing agent is at least one salt of at least one alkali metal in Group IA. In another embodiment, the fluxing agent is at least one salt of at least one alkali metal. In a further embodiment, the at least one alkali metal is sodium. In yet another embodiment, the at least one alkali metal is chosen from alkali metals having a larger atomic radius than that of sodium. In yet a further embodiment, the at least one alkali metal is potassium. In still another embodiment, the at least one alkali metal is rubidium.

The at least one fluxing agent is added to the suspension before spray-drying; as a result, the fluxing agent is located within the wall of the spray-dried granules at locations where it is readily able to provide its fluxing function.

The fluxing agent may be present in the suspension in an amount of less than about 8% based on the total weight of inorganic solids in the suspension, or in an amount of less than about 7%, or an amount of less than about 6%, or in amount of less than about 5%, or in amount of less than about 4%, or in amount of less than about 3%, or in amount less than about 2%. In another embodiment, the suspension contains from about 0.5% to about 10% fluxing agent, based on the total weight of inorganic solids in the suspension.

In some embodiments where the spray-dried granules are flux-calcined, the at least one fluxing agent may undergo a chemical decomposition reaction. In one embodiment of such a chemical decomposition, at least one fluxing agent containing sodium bonds with diatom silica present in the at least one feed material to form sodium silicate, expelling carbon dioxide gas in the process. In another embodiment, at least one fluxing agent containing at least one alkaline metal bonds with diatom silica present in the at least one feed material to form at least one alkaline metal silicate.

The suspension may be spray-dried in a manner which is known per se. The suspension may be fed to the inlet of a spray-dryer and spray-dried material is discharged from the atomiser.

Spray-drying may also be carried out using a nozzle atomiser or fountain spray-drying technique, in which the slurry is sprayed upwards from the cone of the drying chamber.

This allows drying to take place during the complete flight-arc of the droplets before they return to the bottom of the dryer, providing a coarser, more free-flowing powder.

Another type of spray-dryer which may be used in the invention is one which employs a "rotating wheel" or "spinning disc" atomiser. One example of a suitable spray-drying apparatus is a Niro Minor spray dryer unit. This machine has a drying chamber 800 mm in diameter, 600 mm cylindrical height being conical based and is fitted with an air driven disc type atomiser. The atomiser may be run at a speed of 30,000 rpm. Drying may be carried out using an inlet-air temperature of 300° C. Slurry is fed via a peristaltic pump to the atomiser at a rate selected to maintain the required outlet temperature (typically 110 to 120° C.).

In one example of a method of spray-drying, an inlet temperature between 350 and 400° C. and an outlet temperature between 110 and 120° C. was used.

The inorganic solids content of the suspension is dependent on the spray-drying method to be used, which is discussed in more detail below, and the size of spray-dried granules desired. Typically, however, the suspension will have an inorganic solids content of the order of 5 to 30 wt %, for example 15 to 25 wt %.

The heat treatment, also referred to herein as a calcination treatment may be carried out at a suitable temperature to cause mineral particles in the wall of the spray-dried bodies to be sintered together and thus result in a body which is resistant to crushing. The maximum calcination temperature may be for example at least 500° C., or at least 600° C., or at least 700° C., or at least 800° C., or at least 900° C. In order to avoid destroying the fine structure of the spray-dried bodies and incurring additional cost, the maximum calcination temperature is typically less than 1200° C., for example less than 1100° C. or less than 1000° C.

The duration of calcination can be determined empirically depending on the desired outcome. However, typically calcination may be carried out such that the duration at peak temperature is less than four hours, or less than three hours, or less than two hours, or less than one hour. In an embodiment, calcination may be carried out by "flash" calcination, in which the calcination is conducted very rapidly. Calcination may be carried out in a batch process, or in a continuous process. A suitable continuous process may use a rotary tube furnace, in which the uncalcined feed material is continuously passed through a heated zone maintained at the appropriate temperature. In embodiments, the calcination may be carried out by increasing the calcination temperature at a rate of, for example, between 1 and 50° C. per minute, for example 1 to 10° C. per minute, up to the final, maximum temperature and then cooled at a rate of, for example, 1 to 50° C. per minute, for example 5 to 20° C. per minute, to room temperature.

The calcined, spray-dried granulate has substantially the same particle size distribution as the uncalcined starting material.

In certain embodiments, the particulate mineral is agglomerated (granulated) with a binder, wherein one or more smaller particles are attached to form a larger particle. The binder may, for example, be any of the binders described herein, which may also be used for spray drying. For example, the binder may be polyvinyl alcohol. For example, the binder may be partly saponified. For example, the binder may have a viscosity of about 5 cps. For example, the binder may have a % hydrolysation equal to or greater than about 80%, for example equal to or greater than about 85%, for example about 88%. For example, the binder may be Celvol 205E®, available from Sekisui. For example, the binder may be used in an amount equal to or less than about 10% based on the total weight of the particulate mineral. For example, the binder may be used in an amount ranging from about 0.5 to about 8%, for example from about 1 to about 6%, for example from about 1 to about 5%, for example from about 1 to about 3%, based on the total weight of the mineral. For example, the binder may be used in an amount equal to or less than about 5 wt %, for example equal to or less than about 4 wt %, for example equal to or less than about 3 wt %.

In certain embodiments, the particulate mineral may be combined by mixing and/or blending by any technique known to those skilled in the art. The mineral may, for example, be agglomerated by mixing the mineral with a binder, for example using an Eirich mixer or a food mixer (e.g. Hobart food mixer) or using a pelletizer such as a pan pelletizer or drum pelletizer etc. The mineral may, for example, be agglomerated by spray-drying. The mineral may, for example, be agglomerated by spray-drying the binder onto the mineral. For example, a 100 g solution of 3 wt % polyvinyl alcohol may be sprayed onto 100 g of the mineral (e.g. diatomaceous earth). The mineral may, for example, be agglomerated by precipitating the binder onto the mineral in situ. The binder may, for example, be any of the binders described herein, which may also be used for spray drying. In certain embodiments, the binder may, for example, be a precipitated binder. The binder may, for example, be a silica binder. For example, the binder may be an alkali silica binder. For example, the binder may be sodium silicate and/or potassium silicate. For example, the binder may be used in an amount ranging from about 0.5 to about 8%, for example from about 1 to about 6%, for example from about 1 to about 5%, for example from about 1 to about 3%, based on the total weight of the mineral. For example, the binder may be used in an amount equal to or less than about 5 wt %, for example equal to or less than about 4 wt %, for example equal to or less than about 3 wt %.

Before and/or after the agglomeration, the particulate mineral may be subjected to at least one classification step. For example, before and/or after at least one heat treatment, the mineral may, in some embodiments, be subjected to at least one classification step. In some embodiments, the particle size of the particulate mineral is adjusted to a suitable or desired size using any one of several techniques well known in the art. In some embodiments, the mineral is subjected to at least one mechanical separation to adjust the powder size distribution. Appropriate mechanical separation techniques are well known to the skilled artisan and include, but are not limited to, milling, grinding, screening, extrusion, triboelectric separation, liquid classification, aging, and air classification.

The particulate mineral may be subjected to at least one heat treatment. Appropriate heat treatment processes are well-known to the skilled artisan, and include those now known or that may hereinafter be discovered. In some embodiments, the at least one heat treatment decreases the amount of organics and/or volatiles in the heat-treated mineral composition. In some embodiments, the at least one heat treatment includes at least one calcination. In some embodiments, the at least one heat treatment includes at least one flux calcination. In some embodiments, the at least one heat treatment includes at least one roasting.

Calcination may be conducted according to any appropriate process now known to the skilled artisan or hereafter discovered. In some embodiments, calcination is conducted at temperatures below the melting point of the mineral(s). In some embodiments, calcination is conducted at a temperature ranging from about 600° C. to about 1100° C. In some embodiments, the calcination temperature ranges from about 600° C. to about 700° C. In some embodiments, the calcination temperature ranges from about 700° C. to about 800° C. In some embodiments, the calcination temperature ranges from about 800° C. to about 900° C. In some embodiments, the calcination temperature is chosen from the group consisting of about 600° C., about 700° C., about 800° C., about 900° C., about 1000° C., and about 1100° C. Heat treatment at a lower temperature may result in an energy savings over other processes for the preparation of mineral composites.

Flux calcination includes conducting at least one calcination in the presence of at least one fluxing agent. Flux calcination may be conducted according to any appropriate process now known to the skilled artisan or hereafter discovered. In some embodiments, the at least one fluxing agent is any material now known to the skilled artisan or hereafter discovered that may act as a fluxing agent. In some embodiments, the at least one fluxing agent is a salt including at least one alkali metal. In some embodiments, the at least one fluxing agent is chosen from the group consisting of carbonate, silicate, chloride, and hydroxide salts. In other embodiments, the at least one fluxing agent is chosen from the group consisting of sodium, potassium, rubidium, and cesium salts. In still further embodiments, the at least one fluxing agent is chosen from the group consisting of sodium, potassium, rubidium, and cesium carbonate salts.

Roasting may be conducted according to any appropriate process now known to the skilled artisan or hereafter discovered. In some embodiments, roasting is a calcination process conducted at a generally lower temperature that helps to avoid formation of crystalline mineral (e.g. crystalline silica) in the mineral (e.g. diatomaceous earth and/or natural glass). In some embodiments, roasting is conducted at a temperature ranging from about 450° C. to about 900° C. In some embodiments, the roasting temperature ranges from about 500° C. to about 800° C. In some embodiments, the roasting temperature ranges from about 600° C. to about 700° C. In some embodiments, the roasting temperature ranges from about 700° C. to about 900° C. In some embodiments, the roasting temperature is chosen from the group consisting of about 450° C., about 500° C., about 600° C., about 700° C., about 800° C., and about 900° C.

According to some embodiments, the particulate mineral may be subjected to at least one heat treatment, followed by co-agglomerating the heat treated mineral components with at least one binder (e.g. silica binder).

EXAMPLES

Example 1

Experiments were performed to measure the capacity of particulate minerals to absorb/retain chemical compounds present in cigarette smoke. Cigarette smoke is passed through the particulate mineral and filtered on a 0.22 μm filter to prevent biological contamination. The filtered smoke is then bubbled into a liquid ("cigarette extract").

Cigarette extracts were contacted with normal human keratinocytes (NHEK) in culture for 24 hours at various concentrations (pure cigarette extract (100%), 20% cigarette extract (cigarette extract diluted to 1/5), 10%, 2% and 1%). During the last 3 hours, cell proliferation agent WST1 (containing salts of tetrazolium) was introduced and absorbance at 450 nm was measured. The level of yellow colouration is proportional to the number of living cells. The results were presented as graphs showing the % survival (compared to cell culture that was not contacted with cigarette extract) on the y axis and dilution of cigarette extract on the x axis. The analysis of the values was carried out using GraphPad Prism 5 software. A sinusoidal progression analysis evaluated the EC50 for each extract (the concentration of the cigarette extract that induces a response halfway between the baseline (all cells dead) and maximum (all cells alive) after a specified exposure time.

The minerals shown in Table 1 below were tested.

TABLE 1

| Mineral | $d_{50}$ (sedigraph) (μm) | $d_{50}$ (laser) (μm) | Oil Absorption (mL/100 g) | Sebum Absorption (mL/100 g) | Water Absorption (mL/100 g) |
|---|---|---|---|---|---|
| Talc 1 | 3 | 9.5 | 57 | 70 | 70 |
| Perlite | 25 | 26 | 164 | 176 | 242 |
| Kaolin | 0.4 | 1.0 | 50 | 72 | 49 |
| Talc 2 | 2 | 11 | 50 | 52 | 60 |
| DE 1 | 3 | 3 | 90 | 91 | 105 |
| DE 2 | 11 | 11 | 210 | 227 | 267 |

Figure 2:
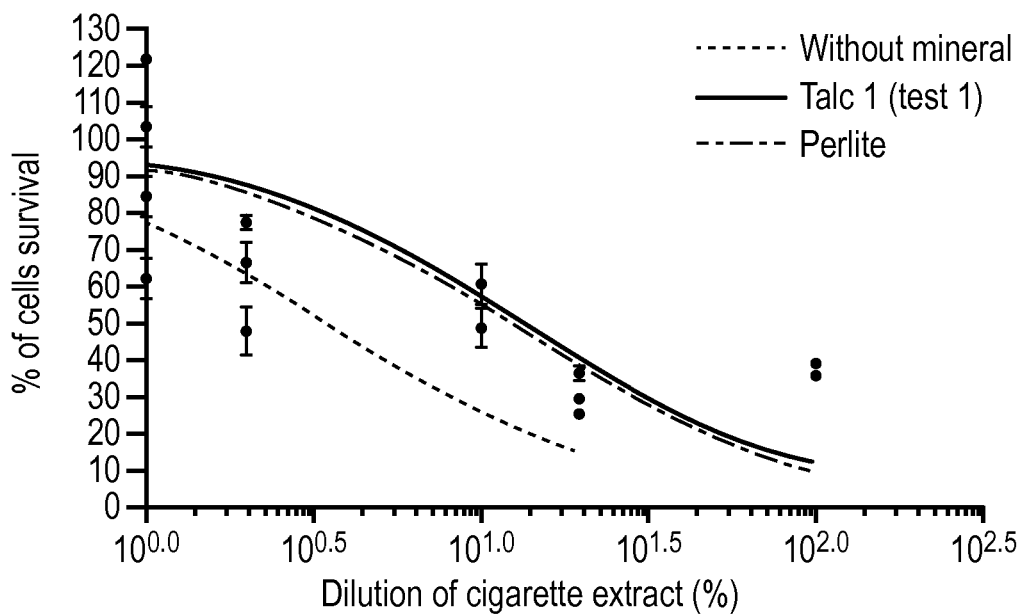
FIG. 2 shows % cell survival vs. cigarette extract dilution (%) when the cigarette extract is filtered through Talc 1 or Perlite in comparison to when the cigarette extract is not filtered through any mineral.
Figure 3:
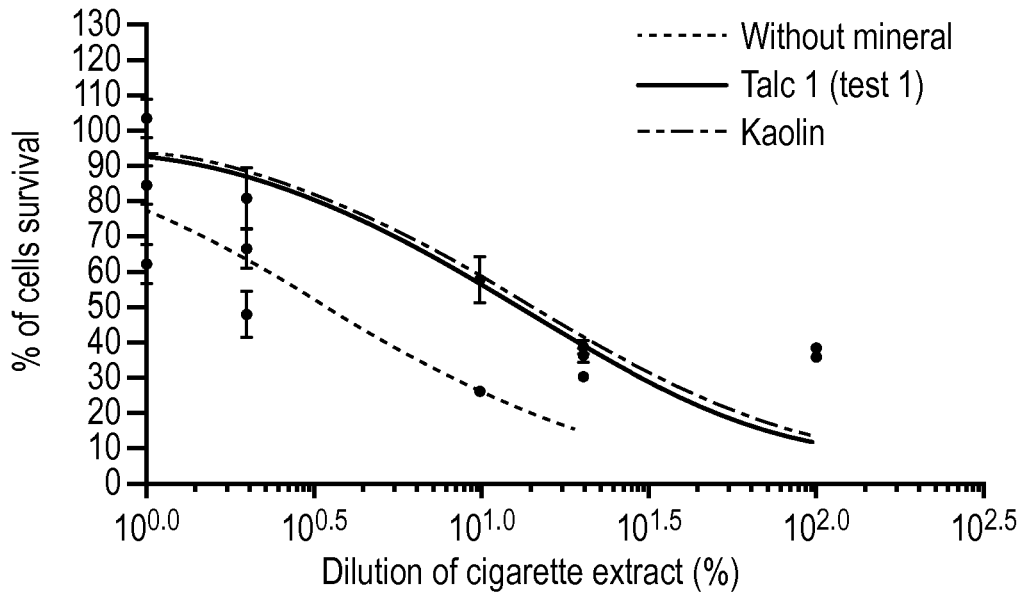
FIG. 3 shows % cell survival vs. cigarette extract dilution (%) when the cigarette extract is filtered through Talc 1 or Kaolin in comparison to when the cigarette extract is not filtered through any mineral.
Figure 4:
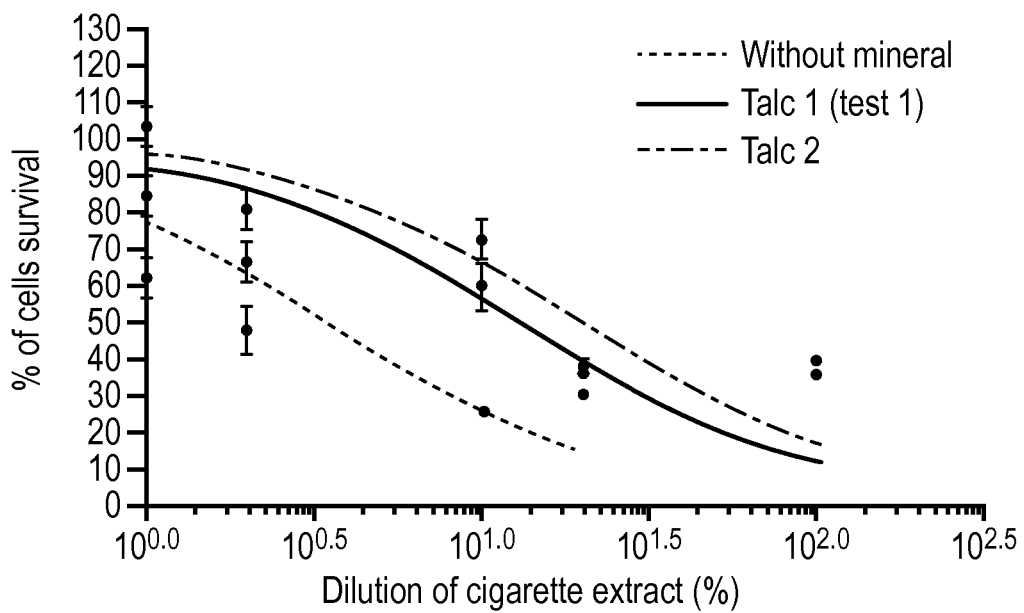
FIG. 4 shows % cell survival vs. cigarette extract dilution (%) when the cigarette extract is filtered through Talc 1 or Talc 2 in comparison to when the cigarette extract is not filtered through any mineral.
Figure 5:
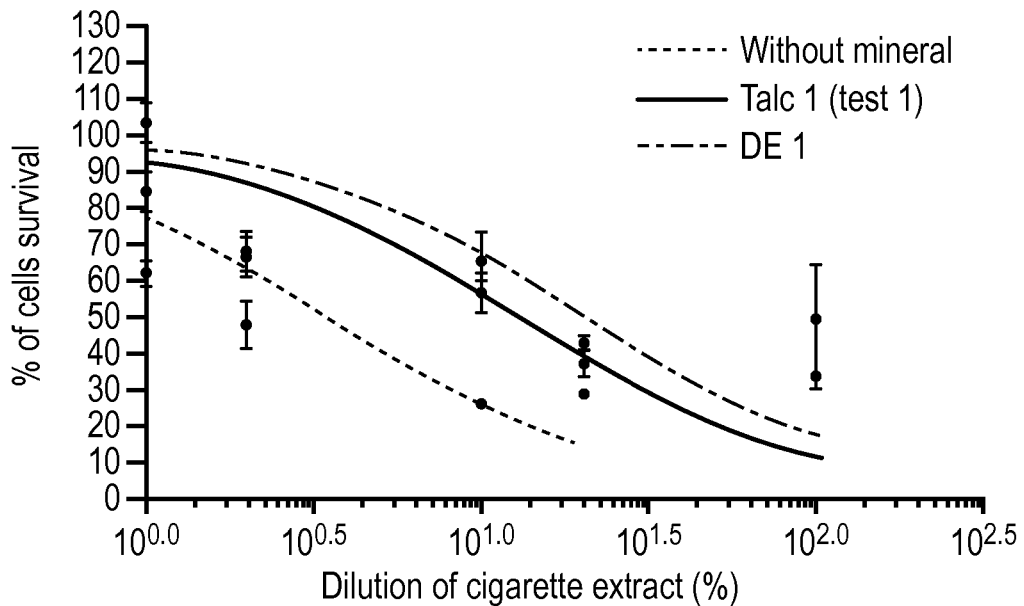
FIG. 5 shows % cell survival vs. cigarette extract dilution (%) when the cigarette extract is filtered through Talc 1 or DE 1 in comparison to when the cigarette extract is not filtered through any mineral.
Figure 6:
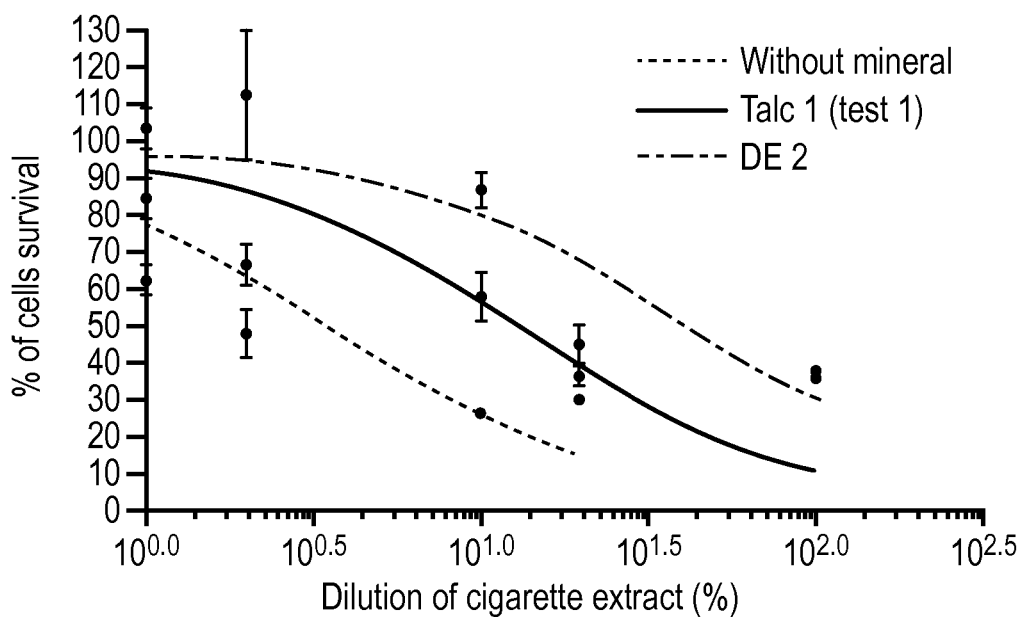
FIG. 6 shows % cell survival vs. cigarette extract dilution (%) when the cigarette extract is filtered through Talc 1 or DE 2 in comparison to when the cigarette extract is not filtered through any mineral.

The results are shown in FIGS. 1 to 6. The EC50 results are shown in Table 2.

TABLE 2

| Mineral | EC50 (%) |
| --- | --- |
| No mineral | 3.4 |
| Talc 1 | 12.4 |
| Perlite | 11.2 |
| Kaolin | 13.8 |
| Talc 2 | 19.9 |
| DE 1 | 40.6 |
| DE 2 | 20.6 |

Example 2

NativeSkin® Plus human skin models were used to test the effect of various minerals on skin exposed to cigarette smoke. The skin models are biopsies of human skin bathed in a nourishing matrix with the epidermal surface in contact with air. A silicone ring allows better application of products and prevents lateral spread of the formulation. The skin biopsies were obtained from the abdominoplasty a 36 year old female and corresponded to a phototype of 3 on the Fitzpatrick scale.

The samples to be tested were applied to the surface of the skin models using a stainless steel spatula in equal amounts. The skin models were then exposed to the smoke of 10 cigarettes before being cleaned with a cotton swab dipped in micellar water and then dried before being placed in an incubator for 24 hours at 37° C. Before exposure to the cigarettes, the samples are homogenously spread on the skin. After exposure, a clogging of the samples is observed.

The skin biopsies were then removed from the matrix and cut into 2 parts, the first part intended for embedding in paraffin and staining as described below, the second part being kept at −80° C. for future studies.

The first part of the skin biopsy was fixed in formalin, dehydrated and then embedded in paraffin. The skin sections had a thickness of 5 μm. The skin sections were stained using Haematoxylin, which makes it possible to analyse the morphology of the skin using a LEICA® DFC 280 microscope. Staining using γH2AX for detecting DNA damage was also performed and observed under a DM5000B microscope. 10 images were obtained for each type of staining. The fluorescence intensity of the γH2AX staining was quantified using Image J analysis and correlated to the percentage of lysed cells.

The test samples were made by mixing talc having a $d_{50}$ of 3.0 μm (sedigraph), an oil absorption of 65 ml/100 g, a BET surface area of 7.5 m$^2$/g and a tapped bulk density (ISO 787/110) of 0.50 g/cm$^3$ with a test mineral and then combining this mineral mixture with a dimethyl polysiloxane base (Dimethisil® DM-200, available from Innospec Performance Chemicals). The relative proportions were 64.4 wt % talc, 27.6 wt % test mineral and 8.0 wt % base.

The test minerals are shown in Table 3. It is noted that Talc 1 is the same talc that is used in combination with the other test minerals in the other test samples.

TABLE 3

| Mineral | $d_{50}$ (sedigraph) (μm) | $d_{50}$ (laser) (μm) | Oil Absorption (mL/100 g) | Sebum Absorption (mL/100 g) | Water Absorption (mL/100 g) |
| --- | --- | --- | --- | --- | --- |
| Talc 1 | 3.00 | 9.5 | 65 | 70 | 70 |
| DE 2 | 11 | 11 | 210 | 227 | 267 |
| Synthetic calcium silicate | — | 19 | 370 | 460 | 400 |
| PCC | 0.07 | 0.07 | 90 | — | 90 |
| DE 3 | — | — | 120 | — | — |

Figure 7:
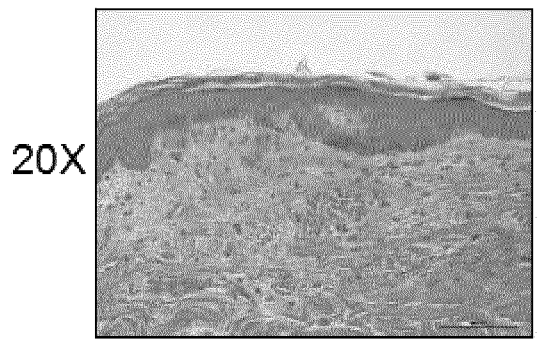
FIG. 7 shows microscope images of skin biopsies that were not exposed to cigarette smoke and had no test sample applied to its surface (top panel) or a test sample containing Talc 1 applied to its surface (bottom panel).
Figure 7:
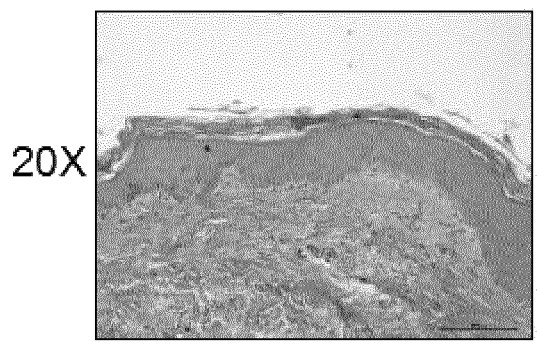
Figure 8:
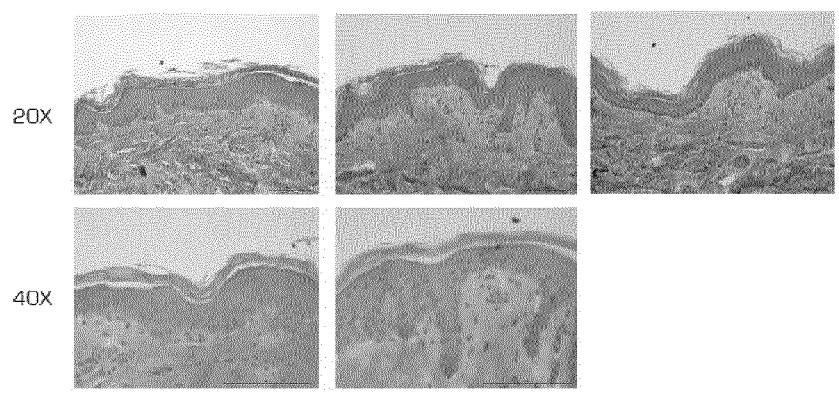
FIG. 8 shows microscope images of skin biopsies that were exposed to no cigarette smoke (first column) or cigarette smoke of 10 cigarettes (second column) where both skin biopsies had a test sample containing Talc 1 applied to its surface, or cigarette smoke of 10 cigarettes (third column) where the skin biopsy had no test sample applied to its surface. The top image is 20× magnification and the bottom image is 40× magnification.
Figure 9:
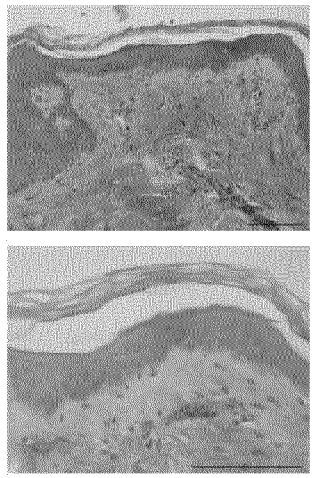
FIG. 9 shows microscope images of skin biopsies that were exposed to cigarette smoke of 10 cigarettes when the skin biopsies had a test sample containing DE 2 applied to its surface. The top image is 20× magnification and the bottom image is 40× magnification.
Figure 10:
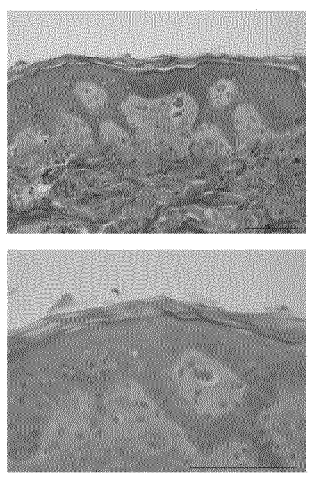
FIG. 10 shows microscope images of skin biopsies that were exposed to cigarette smoke of 10 cigarettes when the skin biopsies had a test sample containing synthetic calcium silicate applied to its surface. The top image is 20× magnification and the bottom image is 40× magnification.
Figure 11:
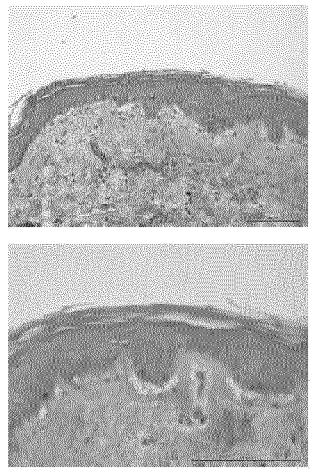
FIG. 11 shows microscope images of skin biopsies that were exposed to cigarette smoke of 10 cigarettes when the skin biopsies had a test sample containing PCC applied to its surface. The top image is 20× magnification and the bottom image is 40× magnification.
Figure 12:
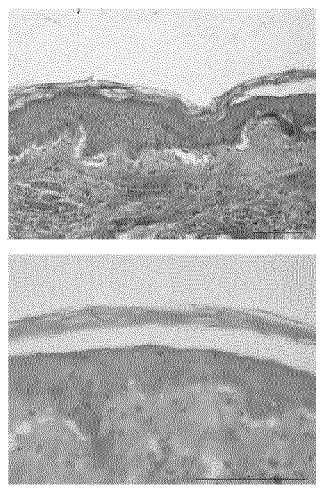
FIG. 12 shows microscope images of skin biopsies that were exposed to cigarette smoke of 10 cigarettes when the skin biopsies had a test sample containing DE 3 applied to its surface. The top image is 20× magnification and the bottom image is 40× magnification.

Images of the skin biopsies stained with Haematoxylin are shown in FIGS. 7 to 12 below.

Skin biopsies that were not exposed to cigarette smoke had a normal morphology whether a test sample was applied or not. No noticeable difference was observed.

For skin biopsies exposed to the smoke of 10 cigarettes, a very important disorganization of the skin layers was observed when no test sample was applied.

A smaller disorganization of the skin layers was observed when test samples containing PCC, DE 3 and synthetic calcium carbonate were applied. No disorganization was observed when test samples containing DE 2 were applied to the skin biopsies.

The results of the quantification of lysed cells by the γH2AX staining method are shown in Table 4. A skin biopsy without having any test sample applied was used as a control.

TABLE 4

| | Test Mineral | % of lysed cells |
| --- | --- | --- |
| No exposure to cigarettes | Control | 0 |
| | Talc 1 | 0 |
| Exposure to 10 cigarettes | Control | 50 |
| | Talc 1 | 28 |
| | DE 2 | 4 |
| | Synthetic calcium silicate | 23 |
| | PCC | 33 |
| | DE 3 | 37 |

The following numbered paragraphs define particular embodiments of the present invention:

1. Use of a particulate mineral as an anti-pollution agent in a composition for application to the skin and/or keratin materials.
2. The use of paragraph 1, wherein the particulate mineral is a silica- or silicate-based mineral.
3. The use of paragraph 1 or 2, wherein the particulate mineral is derived from a natural mineral.
4. The use of any preceding paragraph, wherein the particulate mineral is selected from calcium carbonate, talc, perlite, kaolin, diatomaceous earth and combinations thereof.
5. The use of any preceding paragraph, wherein the particulate mineral has a $d_{50}$ ranging from about 0.5 μm to about 100 μm, for example from about 0.5 μm to about 50 μm, for example from about 0.5 μm to about 30 μm.
6. The use of any preceding paragraph, wherein the particulate mineral has a $d_{10}$ ranging from about 0.05 μm to about 50 μm.
7. The use of any preceding paragraph, wherein the particulate mineral has a $d_{90}$ ranging from about 1 to about 200 μm.

8. The use of any preceding paragraph, wherein the particulate mineral has an oil-absorption capacity equal to or greater than about 20 mL/100 g of the particulate mineral, for example equal to or greater than about 40 mL/100 g of the particulate mineral, for example equal to or greater than about 50 mL/100 g of the particulate mineral, for example equal to or greater than about 80 mL/100 g of the particulate mineral.

9. The use of any preceding paragraph, wherein the particulate mineral has a water-absorption capacity equal to or greater than about 40 mL/100 g of the particulate mineral, for example equal to or greater than about 50 mL/100 g of the particulate mineral, for example equal to or greater than about 100 mL/100 g of the particulate mineral.

10. The use of any preceding paragraph, wherein the particulate mineral has a sebum-absorption capacity equal to or greater than about 30 mL/100 g of the particulate mineral, for example equal to or greater than about 40 mL/100 g of the particulate mineral.

11. The use of any preceding paragraph, wherein the particulate mineral has a L whiteness value equal to or greater than about 80.

12. The use of any preceding paragraph, wherein the use is a cosmetic or therapeutic use.

13. The use of any preceding paragraph, wherein the composition for application to the skin and/or keratin materials is a cosmetic composition such as a hair shampoo, hair conditioner, moisturizer, primer or cleanser.

14. The use of any preceding paragraph, wherein the composition for application to the skin and/or keratin materials is in the form of an emulsion, gel, lotion or cream.

15. The use of any preceding paragraph, wherein the composition for application to the skin and/or keratin material comprises from about 0.5 wt % to about 60 wt % of the particulate mineral.

16. The use of any preceding paragraph, wherein the particulate mineral absorbs pollutants and/or reduces or prevents entry of pollutants into the skin.

17. The use of any preceding paragraph, wherein the composition for application to the skin and/or keratin materials increases cell respiration and/or reduces desquamation and/or inhibits skin aging and/or reduces loss of skin firmness and/or skin elasticity and/or reduce secretion of sebum and/or increase vitamin E levels in the skin.

18. A method for protecting skin and/or keratin materials from pollution, wherein the method comprises applying a composition comprising a particulate mineral to the skin and/or keratin materials.

19. The method of paragraph 18, wherein the particulate mineral is a silica- or silicate-based mineral.

20. The method paragraph 18 or 19, wherein the particulate mineral is derived from a natural mineral.

21. The method of any one of paragraphs 18 to 20, wherein the particulate mineral is selected from calcium carbonate, talc, perite, kaolin, diatomaceous earth and combinations thereof.

22. The method of any one of paragraphs 18 to 21, wherein the particulate mineral has a $d_{50}$ ranging from about 0.5 μm to about 100 μm, for example from about 0.5 μm to about 50 μm, for example from about 0.5 μm to about 30 μm.

23. The method of any one of paragraphs 18 to 22, wherein the particulate mineral has a $d_{10}$ ranging from about 0.05 μm to about 50 μm.

24. The method of any one of paragraphs 18 to 23, wherein the particulate mineral has a $d_{90}$ ranging from about 1 to about 200 μm.

25. The method of any one of paragraphs 18 to 24, wherein the particulate mineral has an oil-absorption capacity equal to or greater than about 20 mL/100 g of the particulate mineral, for example equal to or greater than about 40 mL/100 g of the particulate mineral, for example equal to or greater than about 50 mL/100 g of the particulate mineral, for example equal to or greater than about 80 mL/100 g of the particulate mineral.

26. The method of any one of paragraphs 18 to 25, wherein the particulate mineral has a water-absorption capacity equal to or greater than about 40 mL/100 g of the particulate mineral, for example equal to or greater than about 50 mL/100 g of the particulate mineral, for example equal to or greater than about 100 mL/100 g of the particulate mineral.

27. The method of any one of paragraphs 18 to 26, wherein the particulate mineral has a sebum-absorption capacity equal to or greater than about 30 mL/100 g of the particulate mineral, for example equal to or greater than about 40 mL/100 g of the particulate mineral.

28. The method of any one of paragraphs 18 to 27, wherein the particulate mineral has a L whiteness value equal to or greater than about 80.

29. The method of any one of paragraphs 18 to 28, wherein the use is a cosmetic or therapeutic use.

30. The method of any one of paragraphs 18 to 29, wherein the composition for application to the skin and/or keratin materials is a cosmetic composition such as a hair shampoo, hair conditioner, moisturizer, primer or cleanser.

31. The method of any one of paragraphs 18 to 30, wherein the composition for application to the skin and/or keratin materials is in the form of an emulsion, gel, lotion or cream.

32. The method of any one of paragraphs 18 to 31, wherein the composition for application to the skin and/or keratin material comprises from about 0.5 wt % to about 60 wt % of the particulate mineral.

33. The method of any one of paragraphs 18 to 32, wherein the particulate mineral absorbs pollutants and/or reduces or prevents entry of pollutants into the skin.

34. The method of any one of paragraphs 18 to 33, wherein the composition for application to the skin and/or keratin materials increases cell respiration and/or reduces desquamation and/or inhibits skin aging and/or reduces loss of skin firmness and/or skin elasticity and/or reduce secretion of sebum and/or increase vitamin E levels in the skin.

35. A composition comprising a particulate mineral, wherein the composition can be applied to skin and/or keratin materials to protect the skin and/or keratin materials from pollution.

36. The composition of paragraph 35, wherein the composition is for treatment of dry and/or damaged skin.

37. A method of making a composition of paragraph 35 or 36, wherein the method comprises combining the particulate mineral with a liquid carrier.

The invention claimed is:

1. A method for protecting skin and/or keratin materials from pollution, the method comprising applying a composition comprising a particulate mineral to the skin and/or keratin materials; wherein the particulate mineral comprises from about 5 wt % to about 50 wt % diatomaceous earth, has a $d_{50}$ ranging from about 5 μm to about 15 μm, and has a surface area ranging from about 20 m$^2$/g to about 100 m$^2$/g; wherein the particulate mineral has a sebum-absorption capacity equal to or greater than about 150 mL/100 g of the particulate mineral.

2. The method of claim 1, wherein the particulate mineral has a water-absorption capacity equal to or greater than about 150 mL/100 g of the particulate mineral.

3. The method of claim 1, wherein the composition for application to the skin and/or keratin materials is a cosmetic composition.

4. The method of claim 1, wherein the particulate mineral absorbs pollutants and/or reduces or prevents entry of pollutants into the skin.

5. The method of claim 1, wherein the composition for application to the skin and/or keratin materials is in the form of an emulsion, gel, lotion or cream.

6. The method of claim 1, wherein the composition for application to the skin and/or keratin material comprises from about 5 wt % to about 30 wt % of the particulate mineral.

7. The method of claim 3, wherein the cosmetic composition is chosen from a hair shampoo, hair conditioner, moisturizer, primer, and cleanser.

8. The method of claim 1, wherein the particulate mineral has an oil-absorption capacity equal to or greater than about 150 mL/100 g of the particulate mineral.

9. The method of claim 1, wherein the particulate mineral has an oil-absorption capacity equal to or greater than about 200 mL/100 g of the particulate mineral.

* * * * *